United States Patent [19]
Eriksson et al.

[11] Patent Number: 5,928,939
[45] Date of Patent: Jul. 27, 1999

[54] VASCULAR ENDOTHELIAL GROWTH FACTOR-B AND DNA CODING THEREFOR

[75] Inventors: Ulf Eriksson, Bålsata, Sweden; Birgitta Olofsson, Sundbyberg, Sweden; Kari Alitalo, Helsinki, Sweden; Katri Pajusola, helsinki, Finland

[73] Assignee: Ludwig Institute For Cancer Research, New York, N.Y.

[21] Appl. No.: 08/569,063

[22] Filed: Dec. 6, 1995

Related U.S. Application Data

[63] Continuation-in-part of application No. 08/469,427, Jun. 6, 1995, Pat. No. 5,607,918, which is a continuation-in-part of application No. 08/397,651, Mar. 1, 1995, abandoned.

[51] Int. Cl.⁶ .............................. C12N 5/10; C12N 1/00; C12N 15/12; C12N 15/63
[52] U.S. Cl. ................ 435/325; 435/243; 435/320.1; 435/348; 435/366; 435/410; 536/23.1; 536/23.5; 536/24.33
[58] Field of Search ................... 536/23.1, 23.5, 536/24.3, 24.31, 24.38; 435/320.1, 325, 348, 420, 366, 243, 172.1, 172.3

[56] References Cited

U.S. PATENT DOCUMENTS 5,607,918   3/1997   Eriksson et al. ........................... 514/12

FOREIGN PATENT DOCUMENTS

WO 95/24473   9/1995   WIPO .
WO 96/27007   9/1996   WIPO .
WO 96/39421   12/1996   WIPO .

OTHER PUBLICATIONS

Olofsson et al., "Vascular Endothelial Growth Factor B, a Novel Growth Factor Endothelial Cells", *Proc. Natl. Acad. Sci. USA*, vol. 93, pp. 2576–2581 (1996).

Orlandini et al., "Identification of a c–fos–Induced Gene That is Related to the Platelet–Derived Growth Factor/Vascular Endothelial Growth Factor Family", *Proc. Natl. Acad. Sci. USA*, vol. 93, pp. 11675–11680 (1996).

Ngo et al, The Protein Folding Problem and Tertiary Structure Prediction, Mertz et al (eds.), 1994, Birkhauser, Boston, MA, pp. 433 and 492–495.

*Primary Examiner*—Terry A. McKelvey
*Attorney, Agent, or Firm*—Evenson, McKeown, Edwards & Lenahan, P.L.L.C.

[57] ABSTRACT

VEGF-B polypeptides from the PDGF family of growth factors having the property of promoting mitosis and proliferation of vascular endothelial cells, DNA sequences encoding these polypeptides, pharmaceutical compositions containing them and antibodies which react with them. The VEGF-B polypeptides are useful in stimulating angiogenesis as well as in diagnostic applications.

29 Claims, 9 Drawing Sheets

Figure 1
Deduced amino acid sequence of 1st reading frame of cDNA clone

```
  1                                                                       CG
      Gly Arg Pro Val Val Pro Trp Ile Asp Val Tyr Ala Arg Ala Thr Cys Gln   17
  3   GGA CGC CCA GTG GTG CCA TGG ATA GAC GTT TAT GCA CGT GCC ACA TGC CAG
      Pro Arg Glu Val Val Val Pro Leu Ser Met Glu Leu Met Gly Asn Val Val   34
 55   CCC AGG GAG GTG GTG GTG CCT CTG AGC ATG GAA CTC ATG GGC AAT GTG GTC
      Lys Gln Leu Val Pro Ser Cys Val Thr Val Gln Arg Cys Gly Gly Cys Cys   51
106   AAA CAA CTA GTG CCC AGC TGT GTG ACT GTG CAG CGC TGT GGT GGC TGC TGC
      Pro Asp Asp Gly Leu Glu Cys Val Pro Thr Gly Gln His Gln Val Arg Met   68
157   CCT GAC GAT GGC CTG GAA TGT GTG CCC ACT GGG CAA CAC CAA GTC CGA ATG
      Gln Ile Leu Met Ile Gln Tyr Pro Ser Ser Gln Leu Gly Glu Met Ser Leu   85
208   CAG ATC CTC ATG ATC CAG TAC CCG AGC AGT CAG CTG GGG GAG ATG TCC CTG
      Glu Glu His Ser Gln Cys Glu Cys Arg Pro Lys Lys Lys Arg Arg Val Leu  102
259   GAA GAA CAC AGC CAA TGT GAA TGC AGA CCA AAA AAA AAA AGG AGA GTG CTG
      Stop
310   TGA AGCCAGACAGCCCCAGGATCCTCTGCCCGCCTTGCACCCAGCGCCGTCAACGCCCTGACCCCC
376   GGACCTGCCGCTGCCGCTGCAGACGCCGCCGCTTCCTCCATTGCCAAGGGCGGGGCTTAGAGCTCAA
443   CCCAGACACCTGTAGGTGCCGGAAGCCGCGAAAGTGACAAGCTGCTTTCCAGACTCCACGGGCCCGG
510   CTGCTTTTATGGCCCTGCTTCACAGGGACGAAGAGTGGAGCACAGGCAAACCTCCTCAGTCTGGGAG
577   GTCACTGCCCCAGGACCTGGACCTTTTAGAGAGCTCTCTCGCCATCTTTTATCTCCCAGAGCTGCCA
644   TCTAACAATTGTCAAGGAACCTCATGTCTCACCTCAGGGGCCAGGGTACTCTCTCACTTAACCACCC
711   TGGTCAAGTGAGCATCTTCTGGCTGGCTGTCTCCCCTCACTATGAAAACCCCAAACTTCTACCAATA
778   ACGGGATTTGGGTTCTGTTATGATAACTGTGACACACACACACTCACACTCTGATAAAAGAGAAC
845   TCTGATAAAAGAGATGGAAGACACTAAAAAAAAAAAAAAAAAA
```

(SEQ ID NOS:1 & 2)

Figure 2
Deduced amino acid sequence of 2nd reading frame of cDNA clone.

```
  1                                                              CGGGACGCC
 10   CAGTGGTGCCATGGATAGACGTTTATGCACGTGCCACATGCCAGCCCAGGGAGGTGGTGGTGCCTCT
 77   GAGCATGGAACTCATGGGCAATGTGGTCAAACAACTAGTGCCCAGCTGTGTGACTGTGCAGCGCTGT
144   GGTGGCTGCTGCCCTGACGATGGCCTGGAATGTGTGCCCACTGGGCAACACCAAGTCCGAATGCAGA
211   TCCTCATGATCCAGTACCCGAGCAGTCAGCTGGGGGAGATGTCCCTGGAAGAACACAGCCAATGTGA
                                               Lys Pro Asp Ser Pro Arg      7
278   ATG CAG ACC AAA AAA AAA AAG GAG AGT GCT GTG AAG CCA GAC AGC CCC AGG
      Ile Leu Cys Pro Pro Cys Thr Gln Arg Arg Gln Arg Pro Asp Pro Arg Thr  24
330   ATC CTC TGC CCG CCT TGC ACC CAG CGC CGT CAA CGC CCT GAC CCC CGG ACC
      Cys Arg Cys Arg Cys Arg Arg Arg Arg Phe Leu His Cys Gln Gly Arg Gly  41
381   TGC CGC TGC CGC TGC AGA CGC CGC CGC TTC CTC CAT TGC CAA GGG CGG GGC
      Leu Glu Leu Asn Pro Asp Thr Cys Arg Cys Arg Lys Pro Arg Lys Stop     56
432   TTA GAG CTC AAC CCA GAC ACC TGT AGG TGC CGG AAG CCG CGA AAG TGA CAA
483   GCTGCTTTCCAGACTCCACGGGCCCGGCTGCTTTTATGGCCCTGCTTCACAGGGACGAAGAGTGGAG
550   CACAGGCAAACCTCCTCAGTCTGGGAGGTCACTGCCCCAGGACCTGGACCTTTTAGAGAGCTCTCTC
617   GCCATCTTTTATCTCCCAGAGCTGCCATCTAACAATTGTCAAGGAACCTCATGTCTCACCTCAGGGG
684   CCAGGGTACTCTCTCACTTAACCACCCTGGTCAAGTGAGCATCTTCTGGCTGGCTGTCTCCCCTCAC
751   TATGAAAACCCCAAACTTCTACCAATAACGGGATTTGGGTTCTGTTATGATAACTGTGACACACACA
816   CACACTCACACTCTGATAAAAGAGAACTCTGATAAAAGAGATGGAAGACACTAAAAAAAAAAAAAAA
885   AAA
```

(SEQ ID NOS:1 & 3)

Figure 3
Coding region of clones encoding murine VEGF-B₁₆₇

```
GAGCCCCCTG CTCCGTCGCC TGCTGCTTGT TGCACTGCTG CAGCTGGCTC
GCACCCAGGC CCCTGTGTCC CAGTTTGATG GCCCCAGCCA CCAGAAGAAA
GTGGTGCCAT GGATAGACGT TTATGCACGT GCCACATGCC AGCCCAGGGA
GGTGGTGGTG CCTCTGAGCA TGGAACTCAT GGGCAATGTG GTCAAACAAC
TAGTGCCCAG CTGTGTGACT GTGCAGCGCT GTGGTGGCTG CTGCCCTGAC
GATGGCCTGG AATGTGTGCC CACTGGGCAA CACCAAGTCC GAATGCAGAT
CCTCATGATC CAGTACCCGA GCAGTCAGCT GGGGGAGATG TCCCTGGAAG
AACACAGCCA ATGTGAATGC AGACCAAAAA AAAAGGAGAG TGCTGTGAAG
CCAGACAGCC CCAGGATCCT CTGCCCGCCT TGCACCCAGC GCCGTCAACG
CCCTGACCCC CGGACCTGCC GCTGCCGCTG CAGACGCCGC CGCTTCCTCC
ATTGCCAAGG GCGGGGCTTA GAGCTCAACC CAGACACCTG TAGGTGCCGG
AAGCCGCGAA AGTGA
(SEQ ID NO:4)
```

Figure 4
Deduced amino acid sequence of murine VEGF-B₁₆₇

```
MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
ILMIQYPSSQ LGEMSLEEHS QCECRPKKKE SAVKPDSPRI LCPPCTQRRQ
RPDPRTCRCR CRRRRFLHCQ GRGLELNPDT CRCRKPRK
(SEQ ID NO:5)
```

Figure 5
Coding sequence of clone encoding murine VEGF-B₁₇₄

```
ACCATGAGCC CCTGCTCCG TCGCCTGCTG CTTGTTGCAC TGCTGCAGCT
GGCTCGCACC CAGGCCCCTG TGTCCCAGTT TGATGGCCCC AGCCACCAGA
AGAAAGTGGT GCCATGGATA GACGTTTATG CACGTGCCAC ATGCCAGCCC
AGGGAGGTGG TGGTGCCTCT GAGCATGGAA CTCATGGGCA ATGTGGTCAA
ACAACTAGTG CCCAGCTGTG TGACTGTGCA GCGCTGTGGT GGCTGCTGCC
CTGACGATGG CCTGGAATGT GTGCCCACTG GCAACACCA AGTCCGAATG
CAGGTACCAG GGCTATGGG TCAGATCCTC ATGATCCAGT ACCCGAGCAG
TCAGCTGGGG GAGATGTCCC TGGAAGAACA CAGCCAATGT GAATGCAGAC
CAAAAAAAAA GGAGAGTGCT GTGAAGCCAG ACAGCCCCAG GATCCTCTGC
CCGCCTTGCA CCCAGCGCCG TCAACGCCCT GACCCCGGA CCTGCCGCTG
CCGCTGCAGA CGCCGCCGCT TCCTCCATTG CCAAGGGCGG GGCTTAGAGC
TCAACCCAGA CACCTGTAGG TGCCGGAAGC CGCGAAAGTG A
(SEQ ID NO:6)
```

Figure 6
Deduced amino acid sequence of murine VEGF-B₁₇₄

MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
VPGPMGQILM IQYPSSQLGE MSLEEHSQCE CRPKKKESAV KPDSPRILCP
PCTQRRQRPD PRTCRCRCRR RRFLHCQGRG LELNPDTCRC RKPRK
(SEQ ID NO:7)

Figure 7
Coding region of cDNA encoding murine VEGF-B₁₁₂

ACCATGAGCC CCCTGCTCCG TCGCCTGCTG CTTGTTGCAC TGCTGCAGCT
GGCTCGCACC CAGGCCCCTG TGTCCAGTT TGATGGCCCC AGCCACCAGA
AGAAAGTGGT GCCATGGATA GACGTTTATG CACGTGCCAC ATGCCAGCCC
AGGGAGGTGG TGGTGCCTCT GAGCATGGAA CTCATGGGCA ATGTGGTCAA
ACAACTAGTG CCCAGCTGTG TGACTGTGCA GCGCTGTGGT GGCTGCTGCC
CTGACGATGG CCTGGAATGT GTGCCCACTG GCAACACCA AGTCCGAATG
CAGATCCTCA TGATCCAGTA CCCGAGCAGT CAGCTGGGGG AGATGTCCCT
GGAAGAACAC AGCCAATGTG AATGCAGACC AAAAAAAAAA AGGAGAGTGC
TGTGA
(SEQ ID NO:8)

Figure 8
Deduced amino acid sequence of murine VEGF-B₁₁₂

MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
ILMIQYPSSQ LGEMSLEEHS QCECRPKKKR RVL
(SEQ ID NO:9)

Figure 9
Amino acid sequence alignments of mVEGF-B$_{167}$, mVEGF$_{164}$, hPlGF, mPDGF A and mPDGF B

```
mVEGF-B 167  - - - - - - - - - - - - - - - - - - - - - - - - - - - - - - - -
mVEGF 164    - - - - - - - - - - - - - - - - - - - - - - - - - - - - - - - -
hPlGF        - - - - - - - - - - - - - - - - - - - - - - - - - - - - - - - -
mPDGF A      - M R T W A C L L L L G C G Y L A H A L A E E A E I P R E L
mPDGF B      M N R C W A L F L P L C C Y L R L V S A E G D P I P E E L Y mVEGF-B 167  - - - - - - - - - - - - - - - - - - - M S P L L R R L L
mVEGF 164    - - - - - - - - - - - - - - - M N F L L S W V H W T L A L
hPlGF        - - - - - - - - - - - - - - - M P V M R L F P C F L Q L
mPDGF A      I E R L A R S Q I H S I R D L Q R L L E I D S V G A E D A L
mPDGF B      E M L S D H S I R S F D D L Q R L L H R D S V D E D G A E L mVEGF-B 167  L V A L L Q L A R T Q A P V S Q F D G P S H Q K K V V P W I
mVEGF 164    L L Y L H H A K W S Q A A P - T T E G E Q K S H E V I K F M
hPlGF        L A G L A L P A V P P Q Q W A L S - A G N G S S E V E V V P
mPDGF A      E T S L R A H G S H A I N H V P E K R P V P I R R K R S I E
mPDGF B      D L N M T R A H S G V E L E S S S R G R R S L G S L A A A E mVEGF-B 167  D V Y*A R A T - - C Q P R E V V V P L S M E L M G N V V K Q
mVEGF 164    D V Y Q R S Y - - C R P I E T L V D I F Q E Y P D E I E Y I
hPlGF        F Q E V W G R S Y C R A L E R L V D V V S E Y P S E V E H M
mPDGF A      E A I P A V - - - C K T R T V I Y E I P R S Q V D P T S A N
mPDGF B      P A V I A E - - - C K T R T E V F Q I S R N L I D R T N A N mVEGF-B 167  L - - V P S C V T V Q R C G G C P D D G L E C V P T G Q H
mVEGF 164    E - - K P S C V P L M R C A G C C N D E A L E C V P T S E S
hPlGF        F - - S P S C V S L L R C T G C C G D E N L H C V P V E T A
mPDGF A      F L I W P P C V E V K R C T G C C N T S S V K C Q P S R V H
mPDGF B      F L V W P P C V E V Q R C S G C C N N R N V Q C R A S Q V Q mVEGF-B 167  Q V R M Q I L M I Q Y P S S Q - - - - L G E M S L E E H S Q
mVEGF 164    N I T M Q I M R I K P H Q S Q - - - H I G E M S F L Q H S R
hPlGF        N V T M Q L L K I R S G D R P - - - S Y V E L T F S Q H V R
mPDGF A      H R S V K V A K V E Y V R K K P K L K E V Q V R L E E H L E
mPDGF B      M R P V Q V R K I E I V R K K P I F K K A T V T L E D H L A mVEGF-B 167  C E C R P K K K E S A V K P D S P R I L C P P C T Q R R Q R
mVEGF 164    C E C R P K K D R T - - K P E N H - - - C E P C S E R R K H
hPlGF        C E C R P L R E K M - - K P E - - - - R C G D A V P R R
mPDGF A      C A C A T S N L N P D H R E E E T D V R
mPDGF B      C K C E T I V T P R P V T R S P G T S R E Q R A K T P Q A R mVEGF-B 167  - - - P D P R T C R C R C R R R R F L H C Q G R G L E L N P
mVEGF 164    L F V Q D P Q T C K C S C K N T D - S R C K A R Q L E L N E
hPlGF        
mPDGF A      
mPDGF B      V T I R T V R I R R P P K G K H R K F K H T H D K A A L K E mVEGF-B 167  D T C R C R K P R K
mVEGF 164    R T C R C D K P R R
hPlGF        
mPDGF A      
mPDGF B      T L G A
```

Figure 10
Coding region of a clone encoding human VEGF-B₁₆₇

```
ACCATGAGCC CTCTGCTCCG CCGCCTGCTG CTCGCCGCAC TCCTGCAGCT
GGCCCCCGCC CAGGCCCTG  TCTCCCAGCC TGATGCCCCT GGCCACCAGA
GGAAAGTGGT GTCATGGATA GATGTGTATA CTCGCGCTAC CTGCCAGCCC
CGGGAGGTGG TGGTGCCCTT GACTGTGGAG CTCATGGGCA CCGTGGCCAA
ACAGCTGGTG CCCAGCTGCG TGACTGTGCA GCGCTGTGGT GGCTGCTGCC
CTGACGATGG CCTGGAGTGT GTGCCCACTG GCAGCACCA  AGTCCGGATG
CAGATCCTCA TGATCCGGTA CCCGAGCAGT CAGCTGGGGG AGATGTCCCT
GGAAGAACAC AGCCAGTGTG AATGCAGACC TAAAAAAAAG GACAGTGCTG
TGAAGCCAGA CAGCCCCAGG CCCCTCTGCC CACGCTGCAC CCAGCACCAC
CAGCGCCCTG ACCCCCGGAC CTGCCGCTGC CGCTGCCGAC GCCGCAGCTT
CCTCCGTTGC CAAGGGCGGG GCTTAGAGCT CAACCCAGAC ACCTGCAGGT
GCCGGAAGCT GCGAAGGTGA
(SEQ ID NO:10)
```

Figure 11
Deduced amino acid sequence of human VEGF-B₁₆₇

```
MSPLLRRLLL AALLQLAPAQ APVSQPDAPG HQRKVVSWID VYTRATCQPR
EVVVPLTVEL MGTVAKQLVP SCVTVQRCGG CCPDDGLECV PTGQHQVRMQ
ILMIRYPSSQ LGEMSLEEHS QCECRPKKKD SAVKPDSPRP LCPRCTQHHQ
RPDPRTCRCR CRRRSFLRCQ GRGLELNPDT CRCRKLRR
(SEQ ID NO:11)
```

Figure 12
Nucleotide sequence of coding portion of a cDNA clone encoding murine VEGF-B₁₈₆.

```
ATGAGCCCCC TGCTCCGTCG CCTGCTGCTT GTTGCACTGC TGCAGCTGGC
TCGCACCCAG GCCCTGTGT  CCCAGTTTGA TGGCCCCAGC CACCAGAAGA
AAGTGGTGCC ATGGATAGAC GTTTATGCAC GTGCCACATG CCAGCCCAGG
GAGGTGGTGG TGCCTCTGAG CATGGAACTC ATGGGCAATG TGGTCAAACA
ACTAGTGCCC AGCTGTGTGA CTGTGCAGCG CTGTGGTGGC TGCTGCCCTG
ACGATGGCCT GGAATGTGTG CCCACTGGGC AACACCAAGT CCGAATGCAG
ATCCTCATGA TCCAGTACCC GAGCAGTCAG CTGGGGAGA  TGTCCCTGGA
AGAACACAGC CAATGTGAAT GCAGACCAAA AAAAAGGAG  AGTGCTGTGA
AGCCAGACAG GGTTGCCATA CCCACCACC  GTCCCAGCC  CCGCTCTGTT
CCGGGCTGGG ACTCTACCCC GGGAGCATCC TCCCCAGCTG ACATCATCCA
TCCCACTCCA GCCCCAGGAT CCTCTGCCCG CCTTGCACCC AGCGCCGTCA
ACGCCCTGAC CCCCGGACCT GCCGCTGCCG CTGCAGACGC CGCCGCTTCC
TCCATTGCCA AGGGCGGGGC TTAG
(SEQ ID NO:12)
```

Figure 13
Deduced amino acid sequence of murine VEGF-B$_{186}$.

```
MSPLLRRLLL VALLQLARTQ APVSQFDGPS HQKKVVPWID VYARATCQPR
EVVVPLSMEL MGNVVKQLVP SCVTVQRCGG CCPDDGLECV PTGQHQVRMQ
ILMIQYPSSQ LGEMSLEEHS QCECRPKKKE SAVKPDRVAI PHHRPQPRSV
PGWDSTPGAS SPADIIHPTP APGSSARLAP SAVNALTPGP AAAAADAAAS
SIAKGGA
(SEQ ID NO:13)
```

Figure 14
Nucleotide sequence of coding portions of a cDNA clone H.1 encoding human VEGF-B$_{186}$.

```
ATGAGCCCTC TGCTCCGCCG CCTGCTGCTC GCCGCACTCC TGCAGCTGGC
CCCCGCCCAG GCCCCTGTCT CCCAGCCTGA TGCCCCTGGC CACCAGAGGA
AAGTGGTGTC ATGGATAGAT GTGTATACTC GCGCTACCTG CCAGCCCCGG
GAGGTGGTGG TGCCCTTGAC TGTGGAGCTC ATGGGCACCG TGGCCAAACA
GCTGGTGCCC AGCTGCGTGA CTGTGCAGCG CTGTGGTGGC TGCTGCCCTG
ACGATGGCCT GGAGTGTGTG CCCACTGGGC AGCACCAAGT CCGGATGCAG
ATCCTCATGA TCCGGTACCC GAGCAGTCAG CTGGGGGAGA TGTCCCTGGA
AGAACACAGC CAGTGTGAAT GCAGACCTAA AAAAAAGGAC AGTGCTGTGA
AGCCAGACAG GGCTGCCACT CCCCACCACC GTCCCCAGCC CCGTTCTGTT
CCGGGCTGGG ACTCTGCCCC CGGAGCACCC TCCCCAGCTG ACATCACCCA
TCCCACTCCA GCCCCAGGCC CCTCTGCCCA CGCTGCACCC AGCACCACCA
GCGCCCTGAC CCCCGGACCT GCCGCCGCCG CTGCCGACGC CGCAGCTTCC
TCCGTTGCCA AGGGCGGGGC TTAG
(SEQ ID NO:14)
```

Figure 15
Deduced amino acid sequence of human VEGF-B$_{186}$.

```
MSPLLRRLLL AALLQLAPAQ APVSQPDAPG HQRKVVSWID VYTRATCQPR
EVVVPLTVEL MGTVAKQLVP SCVTVQRCGG CCPDDGLECV PTGQHQVRMQ
ILMIRYPSSQ LGEMSLEEHS QCECRPKKKD SAVKPDRAAT PHHRPQPRSV
PGWDSAPGAP SPADITHPTP APGPSAHAAP STTSALTPGP AAAAADAAAS
SVAKGGA
(SEQ ID NO:15)
```

```
mVEGF-B 167  MSPLLRRLLLVALLQLARTQAPVSQFDGPS   30
hVEGF-B 167  MSPLLRRLLLAALLQLAPAQAPVSQPDAPG   30
mVEGF-B 186  MSPLLRRLLLVALLOLARTQAPVSQFDGPS   30
hVEGF-B 186  MAPLLRRLLLAALLOLAPAQAPVSQPDAPG   30 mVEGF-B 167  HQKKVVPWISVYARATCQPREVVVPLSMEL   60
hVEGF-B 167  HQRKVVSWIDVYTRATCQPREVVVPLTVEL   60
mVEGF-B 186  HQKKVVPWIDVYARATCQPREVVVPLSMEL   60
hVEGF-B 186  HQRKVVSWIDVYTRATCQPREVVVPLTVEL   60 mVEGF-B 167  MGNVVKQLVPSCVTVQRCGGCCPDDGLECV   90
hVEGF-B 167  MGTVAKQLVPSCVTVQRCGGCCPDDGLECV   90
mVEGF-B 186  MGNVVKQLVPSCVTVQRCGGCCPDDGLECV   90
hVEGF-B 186  MGTVAKQLVPSCVTVQRCGGCCPDDGLECV   90 mVEGF-B 167  PTGQHQVRMQILMIQYPSSQLGEMSLEEHS  120
hVEGF-B 167  PTGQHQVRMQILMIRYPSSQLGEMSLEEHS  120
mVEGF-B 186  PTGQHQVRMQILMIQYPSSQLGEMSLEEHS  120
hVEGF-B 186  PTGQHQVRMQILMIRYPSSQLGEMSLEEHS  120 mVEGF-B 167  QCECRPKKKESAVKPDSPRILCPPCTQRRQ  150
hVEGF-B 167  QCECRPKKKDSAVKPDSPRPLCPRCTQHHQ  150
mVEGF-B 186  QCECRPKKKESAVKPDRVAIPHHRPQPRSV  150
hVEGF-B 186  QCECRPKKKDSAVKPDRAATPHHRPQPRSV  150 mVEGF-B 167  RPDPRTCRCRCRRRRFLHCQGRGLELNPDT  180
hVEGF-B 167  RPDPRTCRCRCRRRSPLRCQGRGLELNPDT  180
mVEGF-B 186  PGWDSTPGASSPADIIHPTPAPGSSARLAP  180
hVEGF-B 186  PGWDSAPGAPSPADITHPTPAPGPSAHAAP  180 mVEGF-B 167  CRCRKPRK                        188
hVEGF-B 167  CRCRKLRR                        188
mVEGF-B 186  SAVNALTPGPAAAAADAAASSIAKGGA    207
hVEFG-B 186  STTSALTPGPAAAAADAAASSVAKGGA    207
```

FIG. 16

Phylogenetic analysis of the VEGF-PDGF family of growth factors

Number of Substitution Events

Induction of [$^3$H]thymidine by VEGF-B

VASCULAR ENDOTHELIAL GROWTH FACTOR-B AND DNA CODING THEREFOR

CROSS-REFERENCE TO RELATED APPLICATION

This application is a continuation-in-part of U.S. Pat. No. 5,607,918, application Ser. No. 08/469,427, filed Jun. 6, 1995, which in turn is a continuation-in-part of application Ser. No. 08/397,651, filed Mar. 1, 1995, now abandoned.

BACKGROUND OF THE INVENTION

Angiogenesis, or the proliferation of new capillaries from pre-existing blood vessels, is a fundamental process necessary for normal growth and development of tissues. It is a prerequisite for the development and differentiation of the vascular tree, as well as for a wide variety of fundamental physiological processes including embryogenesis, somatic growth, tissue and organ repair and regeneration, cyclical growth of the corpus luteum and endometrium, and development and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, e.g. in the healing of wounds and fractures. Angiogenesis is also a factor in tumor growth, since a tumor must continuously stimulate growth of new capillary blood vessels in order to grow.

Capillary blood vessels consist of endothelial cells and pericytes. These two cell types carry all of the genetic information to form tubes, branches and entire capillary networks. Specific angiogenic molecules can initiate this process. In view of the physiological importance of angiogenesis, much effort has been devoted to the isolation, characterization and purification of factors that can stimulate angiogenesis. A number of polypeptides which stimulate angiogenesis have been purified and characterized as to their molecular, biochemical and biological properties. For reviews of such angiogenesis regulators, see Klagsbrun et al., "Regulators of Angiogenesis", *Ann. Rev. Physiol.*, 53:217–39 (1991); and Folkman et al., "Angiogenesis," *J. Biol. Chem.*, 267:10931–934 (1992). Recent results have implicated several endothelial receptor tyrosine kinases (RTKs) in the establishment and maintenance of the vascular system.

One such growth factor, which is highly specific as a mitogen for vascular endothelial cells, is termed vascular endothelial growth factor (VEGF). See Ferrara et al., "The Vascular Endothelial Growth Factor Family of Polypeptides," *J. Cellular Biochem.*, 47:211–218 (1991); Connolly, "Vascular Permeability Factor: A Unique Regulator of Blood Vessel Function," *J. Cellular Biochem.*, 47:219–223 (1991). VEGF is a potent vasoactive protein that has been detected in media conditioned by a number of cell lines including bovine pituitary follicular cells. VEGF is a glycosylated cationic 46–48 kD dimer made up of two 24 kD subunits. It is inactivated by sulfhydryl reducing agents, resistant to acidic pH and to heating, and binds to immobilized heparin. VEGF is sometimes referred to as vascular permeability factor (VPF) because it increases fluid leakage from blood vessels following intradermal injection. It also has been called by the name vasculotropin.

Four different molecular species of VEGF have been detected. The 165 amino acid species has a molecular weight of approximately 46 kD and is the predominant molecular form found in normal cells and tissues. A less abundant, shorter form with a deletion of 44 amino acids between positions 116 and 159 ($VEGF_{121}$) a longer form with an insertion of 24 highly basic residues in position 116 ($VEGF_{189}$), and another longer form with an insertion of 41 amino acids ($VEGF_{206}$), which includes the 24 amino acid insertion found in $VEGF_{189}$, are also known. $VEGF_{121}$ and $VEGF_{165}$ are soluble proteins. $VEGF_{189}$ and $VEGF_{206}$ appear to be mostly cell-associated. All of the versions of VEGF are biologically active. For example, each of the species when applied intradermally is able to induce extravasation of Evans blue.

The various species of VEGF are encoded by the same gene and arise from alternative splicing of messenger RNA. This conclusion is supported by Southern blot analysis of human genomic DNA, which shows that the restriction pattern is identical using either a probe for $VEGF_{165}$ or one which contains the insertion in $VEGF_{206}$. Analysis of genomic clones in the area of putative mRNA splicing also shows an intron/exon structure consistent with alternative splicing.

Analysis of the nucleotide sequence of the VEGF gene indicates that VEGF is a member of the platelet-derived growth factor (PDGF) family. VEGF and PlGF are ligands for two endothelial RTKs, flt-1 (VEGF receptor 1, VEGFR1) and flk-1/KDR (VEGF receptor 2, VEGFR2). The amino acid sequence of VEGF exhibits approximately 20% homology to the sequences of the A and B chains of PDGF, as well as complete conservation of the eight cysteine residues found in both mature PDGF chains. $VEGF_{165}$, $VEGF_{189}$ and $VEGF_{206}$ also contain eight additional cysteine residues within the carboxy-terminal region. The amino-terminal sequence of VEGF is preceded by 26 amino acids corresponding to a typical signal sequence. The mature protein is generated directly following signal sequence cleavage without any intervening prosequence. The existence of a potential glycosylation site at $Asn^{74}$ is consistent with other evidence that VEGF is a glycoprotein, but the polypeptide has been reported to exist in both glycosylated and deglycosylated species.

Like other cytokines, VEGF can have diverse effects that depend on the specific biological context in which it is found. VEGF and its high affinity receptors flt-1 and KDR/flk-1 are required for the formation and maintenance of the vascular system as well as for both physiological and pathological angiogenesis. VEGF is a potent endothelial cell mitogen and directly contributes to induction of angiogenesis in vivo by promoting endothelial cell growth during normal development or during wound healing. A most striking property of VEGF is its specificity. It is mitogenic in vitro at 1 ng/ml for capillary and human umbilical vein endothelial cells, but not for adrenal cortex cells, corneal or lens epithelial cells, vascular smooth muscle cells, corneal endothelial cells, granulosa cells, keratinocytes, BHK-21 fibroblasts, 3T3 cells, rat embryo fibroblasts, human placental fibroblasts and human sarcoma cells. The target cell specificity of VEGF is thus restricted to vascular endothelial cells. VEGF can trigger the entire sequence of events leading to angiogenesis and stimulates angiogenesis in vivo in the cornea and in a healing bone graft model. It is able to stimulate the proliferation of endothelial cells isolated from both small and large vessels. Expression of VEGF mRNA is temporally and spatially related to the physiological proliferation of capillary blood vessels in the ovarian corpus luteum or in the developing brain. VEGF expression is triggered by hypoxemia so that endothelial cell proliferation and angiogenesis appear to be especially stimulated in ischemic areas. VEGF is also a potent chemoattractant for monocytes. In addition, VEGF induces plasminogen activator and plasminogen activator inhibitor in endothelial cells.

Tumor cells release angiogenic molecules such as VEGF, and monoclonal antibodies to VEGF have been shown to inhibit the growth of certain types of tumor such as rhabdomyosarcoma. See Kim et al., "Inhibition of Vascular Endothelial Growth Factor-Induced Angiogenesis Suppresses Tumor Growth in vivo," Nature, 362:841–844 (1993). This suggests that blocking VEGF action is of potential therapeutic significance in treating tumors in general, and highly-vascularized, aggressive tumors in particular.

SUMMARY OF THE INVENTION

It is an object of the invention to provide a new growth factor having the property of promoting proliferation of endothelial cells.

Another object of the invention is to provide isolated DNA sequences which encode a new growth factor which promotes proliferation of endothelial cells.

It is also an object of the invention to provide new products which may be useful in diagnostic and/or therapeutic applications.

These and other objects are achieved in accordance with the present invention by providing an isolated DNA which codes for a protein exhibiting the following characteristic amino acid sequence Pro-Xaa-Cys-Val-Xaa-Xaa-Xaa-Arg-Cys-Xaa-Gly-Cys-Cys (SEQ ID NO:16) and having the property of promoting proliferation of endothelial cells or mesodermal cells, the DNA being selected from the group consisting of the DNA of FIGS. 1 and 2 (SEQ ID NO:1), the DNA of FIG. 3 (SEQ ID NO:4), the DNA of FIG. 5 (SEQ ID NO:6); the DNA of FIG. 7 (SEQ ID NO:8), the DNA of FIG. 10 (SEQ ID NO:10), the DNA of FIG. 12 (SEQ ID NO:12), the DNA of FIG. 14 (SEQ ID NO:14), and DNA's which hybridize under stringent conditions with at least one of the foregoing DNA sequences.

In accordance with further aspects of the invention, the objects are also achieved by providing a protein exhibiting the following characteristic amino acid sequence Pro-Xaa-Cys-Val-Xaa-Xaa-Xaa-Arg-Cys-Xaa-Gly-Cys-Cys (SEQ ID NO:16) and having the property of promoting proliferation of endothelial cells or mesodermal cells, which protein comprises a sequence of amino acids substantially corresponding to an amino acid sequence selected from the group consisting of the amino acid sequence of FIG. 1 (SEQ ID NO:2), the amino acid sequence of FIG. 2 (SEQ ID NO:3), the amino acid sequence of FIG. 4 (SEQ ID NO:5), the amino acid sequence of FIG. 6 (SEQ ID NO:7), the amino acid sequence of FIG. 8 (SEQ ID NO:9), the amino acid sequenc of FIG. 11 (SEQ ID NO:11), the amino acid sequence of FIG. 13 (SEQ ID NO:13), and the amino acid sequence of FIG. 15 (SEQ ID NO:15).

In further aspects of the invention, the objects are achieved by providing pharmaceutical preparations which comprise such proteins; and by providing antibodies which react with such proteins.

The novel growth factor of the present invention, referred to hereinafter as vascular endothelial growth factor B or VEGF-B, has close structural similarities to VEGF and to placenta growth factor (PlGF). All of the VEGF-B forms contain the characteristic amino acid sequence Pro-Xaa-Cys-Val-Xaa-Xaa-Xaa-Arg-Cys-Xaa-Gly-Cys-Cys (SEQ ID NO:16) (wherein Xaa represents a variable residue), which is an earmark of the PDGF/VEGF family of growth factors. This characteristic amino acid sequence can be found at amino acids 70 to 82 in FIGS. 4, 6, 8, 11, 13 and 15.

Clinical applications of the invention include diagnostic applications, acceleration of angiogenesis in wound healing, and inhibition of angiogenesis. Quantitation of VEGF-B in cancer biopsy specimens may be useful as an indicator of future metastatic risk. Topical application of VEGF-B preparations to chronic wounds may accelerate angiogenesis and wound healing.

BRIEF DESCRIPTION OF THE DRAWINGS

FIG. 1 shows the nucleotide sequence of the (partial) cDNA clone of VEGF-B (SEQ ID NO:1) and the amino acid sequence of the protein segment (SEQ ID NO:2) coded by the first reading frame of the cDNA;

FIG. 2 repeats the nucleotide sequence of the (partial) cDNA clone of VEGF-B (SEQ ID NO:1) and the amino acid sequence of the protein segment (SEQ ID NO:3) coded by the second reading frame of the cDNA;

FIG. 3 shows the nucleotide sequence of the coding region of a full length cDNA clone of VEGF-$B_{167}$ (SEQ ID NO:4);

FIG. 4 shows the amino acid sequence of VEGF-$B_{167}$ (SEQ ID NO:5);

FIG. 5 shows the nucleotide sequence of the coding region of a cDNA clone of VEGF-$B_{174}$ (SEQ ID NO:6);

FIG. 6 shows the amino acid sequence of VEGF-$B_{174}$ (SEQ ID NO:7);

FIG. 7 shows the nucleotide sequence of a cDNA clone of VEGF-$B_{112}$ (SEQ ID NO:8);

FIG. 8 shows the amino acid sequence of VEGF-$B_{112}$ (SEQ ID NO:9);

FIG. 9 shows a comparison of the amino acid sequences of mVEGF-$B_{167}$(SEQ ID NO:5), mVEGF$_{164}$(SEQ ID NO:20), hPlGF (SEQ ID NO:21), mPDGF A (SEQ ID NO:22), and mPDGF B (SEQ ID NO:23);

FIG. 10 shows the nucleotide sequence of a clone of human VEGF-$B_{167}$ (SEQ ID NO:10);

FIG. 11 shows the amino acid sequence of human VEGF-$B_{167}$ (SEQ ID NO:11); and FIG. 12 shows the nucleotide sequence of murine VEGF-$B_{186}$ (SEQ ID NO:12);

FIG. 13 shows the amino acid sequence of murine VEGF-$B_{186}$ (SEQ ID NO:13);

FIG. 14 shows the nucleotide sequence of human VEGF-$B_{186}$ (SEQ ID NO:14);

FIG. 15 shows the amino acid sequence of human VEGF-$B_{186}$ (SEQ ID NO:15);

FIG. 16 shows an amino acid sequence comparison of murine and human VEGF-$B_{167}$ and VEGF-$B_{186}$ isoforms (SEQ ID NOS:5, 11 13 and 15).

DETAILED DESCRIPTION OF PREFERRED EMBODIMENTS

Figure 17:
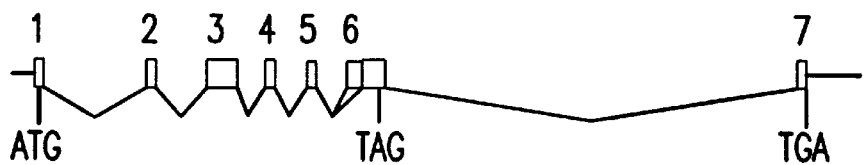
FIG. 17 shows the schematic structure of mouse and human genes for VEGF-B.

The present invention thus is directed to new vascular endothelial growth factors, hereinafter referred to as VEGF-B growth factors, which share the angiogenic and other properties of VEGF, but which are distributed and expressed in tissues differently from VEGF.

VEGF-B growth factors are members of the family of platelet derived growth factors and are a growth factors which promote mitosis and proliferation of vascular endothelial cells and/or mesodermal cells. They are produced by expression of DNA sequences which correspond to, or which are hybridizable under stringent conditions with, any one of the DNA sequences depicted in FIGS. 1 and 2 (SEQ ID NO:1), FIG. 3 (SEQ ID NO:4), FIG. 5 (SEQ ID NO:6), FIG. 7 (SEQ ID NO:8), FIG. 10 (SEQ ID NO:10), FIG. 12 (SEQ ID NO:12) or FIG. 14 (SEQ ID NO:14). It is intended to include within the scope of the invention all angiogenic proteins encoded by DNA sequences which hybridize under stringent conditions to any one of the foregoing DNA sequences. Suitable hybridization conditions include, for example, 50% formamide, 5× SSPE (=0.9M sodium chloride, 0.05M sodium phosphate, pH 7.7 and 0.005M ethylene diamine tetraacetic acid (EDTA)) buffer, 5× Denhardts solution, 0.5% SDS (=sodium dodecyl sulfate) and 100 µg/ml of salmon sperm DNA at 42° C. overnight, followed by washing 2×30 minutes in 2× SSC (=0.75M sodium chloride and 0.075M sodium citrate) at 55° C.

The invention is also directed to an isolated and/or purified DNA which corresponds to, or which hybridizes under stringent conditions with, any one of the foregoing DNA sequences.

In a further aspect, the invention is directed to antibodies of VEGF-B growth factors, and particularly to monoclonal antibodies.

VEGF-B proteins are believed to interact with protein tyrosine kinase growth factor receptors. Details of such receptors are known in the art [See e.g. Wilks, A. F., "Protein Tyrosine Kinase Growth Factor Receptors and Their Ligands in Development, Differentiation, and Cancer," *Adv. Cancer Res.*, 60:43–73 (1993)].

Various adult mouse tissues were tested for expression of transcripts corresponding to VEGF-B by Northern blotting. The size of the mRNA was 1.3–1.4 kb. A mouse multiple tissue Northern blot (MTN, Clontech) was probed with the 0.89 kb SalI-NotI fragment derived from the pPC67 yeast expression vectors described above. The probe was labelled with $^{32}$P-dCTP using random priming (specific activity $10^8$–$10^9$ cpm/µg of DNA). The blot was hybridized overnight at 42° C. using 50% formamide, 5× SSPE buffer, 2% SDS, 10× Denhardts solution, 100 µg/ml salmon sperm DNA and 1×10$^6$ cpm of the labelled probe/ml. The blot was washed at room temperature for 2×30 min in 2× SSC containing 0.05% SDS and then for 2×20 min at 52° C. in 0.1× SSC containing 0.1% SDS. The blot was then exposed at −70° C. for three days using intensifying screens. Kodak XAR film was used. The relative expression levels as determined by visual examinations of the film are listed in the following table:

TABLE 1

Distribution of VEGF-B Transcripts in the Adult Mouse

| Tissue | Relative Expression Level |
|---|---|
| Heart | +++++ |
| Brain | +++ |
| Spleen | (+) |
| Lung | ++ |
| Liver | + |
| Skeletal Muscle | ++++ |
| Kidney | +++ |
| Testis | (+) |

+++++ = very strong expression; ++++ = strong expression; +++ = moderate expression; ++ = rather weak expression; + = weak expression; (+) = very weak expression.

A human multiple tissue Northern blot (MNT) from Clontech was probed using the murine partial cDNA to determine relative VEGF-B expression levels in various human tissues. The size of the transcript was 1.3–1.4 kb. The conditions were identical to those used for the mouse Northern blot described above. The relative VEGF-B transcript levels for the human Northern blot are listed in the following Table 2. For comparison purposes, Table 2 also lists relative expression level data from the literature for VEGF in various mammalian systems.

TABLE 2

| | Relative Expression Levels | | | |
|---|---|---|---|---|
| | VEGF-B (Northern blot) | VEGF (from literature) | | |
| Tissues | human | human | murine | guinea pig |
| heart | +++++ | ++ | +++ | +++ |
| brain | + | | + | + |
| placenta | + | | | |
| lung | + | ++++ | | ++ |
| liver | (+) | ++ | (+) | + |
| skeletal muscle | ++++ | | +++ | + |
| kidney | + | ++ | + | ++ |
| pancreas | +++ | | | |
| spleen | ++ | | − | + |
| thymus | + | | − | |
| prostate | +++ | | | |
| testis | ++ | | | (+) |
| ovary | +++ | | | − |
| small intestine | ++ | | | |
| colon | +++ | | | |
| peripheral blood leucocytes | + | | | |

From a comparison of Table 1 and Table 2 it can be seen that mouse and human tissue expression levels of VEGF-B transcripts are relatively similar with the highest expression levels being found in heart and skeletal muscle. Significant differences may be seen in brain and kidney tissue. It should also be noted that tissues containing a large proportion of both muscular and epithelial cells, such as prostate, pancreas and colon from which some of the most common human tumors originate, express relatively high levels of VEGF-B.

A comparison of the relative expression levels of VEGF and VEGF-B in human tissues shows some striking differences. VEGF is expressed rather weakly by human heart tissue, but VEGF-B is very strongly expressed by the same tissue. On the other hand, VEGF is strongly expressed by human lung tissue, but VEGF-B is only weakly expressed by human lung tissue. In a similar vein, human liver tissue expresses VEGF at a moderate level, but VEGF-B is expressed only very weakly. These data evidence that despite their general similarities, the actions of VEGF and VEGF-B are not completely identical.

The expression of VEGF-B transcripts was further analyzed in mouse and human tissues by Northern blotting and compared with the expression of VEGF transcripts. Mouse and human multiple tissue Northern (MTN) blots (Clontech) were hybridized with a 32P-labelled mouse VEGF-B probe (0.9 kb Sal I/Not I insert of the clone pcif 2). VEGF expression was analysed with $^{32}$P-labelled VEGF$_{165}$ cDNA as the probe. The hybridizations were carried out at 42° C. in 50% deionized formamide, 5× SSC pH 7.0, 1% SDS, 5× Denhardt's solution and 100 μg/ml of denatured salmon sperm DNA. The filters were washed 2×30 min at 52° C. in 2× SSC containing 0.5% SDS and exposed to Kodak XAR film for 2–5 days at −70° C. using intensifying screens. In situ hybridization analysis of adult mouse tissues from CBA mice and of embryos derived from matings of CBA and NMRI mice were carried out essentially as previously described by Korhonen et al., *Blood*, 80, 2548–55 (1992). The RNA probes (a 383 bp antisense probe and a 169 bp sense probe) were generated from a linearized plasmid containing a 440 bp Sal I/Sac I fragment derived from the pcif 2 cDNA clone. Radiolabelled RNA was synthesized using T7 and SP6 RNA polymerases and [$^{35}$S]UTP (Amersham Inc.). Alkaline hydrolysis of the probes was omitted. Hematoxylin was used for counterstaining. Control hybridizations with sense strand and RNAse A-treated sections did not give signals above background.

In mouse tissues the most abundant expression of the 1.4 kb VEGF-B transcript was detected in heart, brain, skeletal muscle, and kidney. The major 3.7 kb VEGF transcript was is expressed in heart, brain, lung, skeletal muscle and kidney. In human tissues, the most abundant expression of the 1.4 kb VEGF-B transcript and the major 3.7 and 4.5 kb VEGF transcripts were detected in heart, skeletal muscle, pancreas and prostate. Thus, although clear quantitative differences exist, it appears that VEGF-B and VEGF are coexpressed in many human and mouse tissues.

The expression of VEGF-B transcripts was further examined by in situ hybridization in sections from adult mouse heart and skeletal muscle and from the early (E 10) mouse embryo. In the adult heart, VEGF-B transcripts are prominently expressed in the myocardium, while no specific signal is detected in arterial smooth muscle. In adult striated muscle, VEGF-B transcripts are expressed by some of the myofibers whereas others seem to lack the transcript. In the E 10 mouse embryo, VEGF-B transcripts are detected mainly in the developing heart. The myocardium of the adult mouse heart has a prominent signal. In striated muscle, VEGF-B expression is seen in subpopulations of myofibers. Strong signals were also obtained in the developing heart of the E10 mouse embryo. Other embryonic structures expressed lower or undetectable levels of transcripts for VEGF-B. Taken together, these tests indicate that VEGF-B transcrips are expressed primarily in muscular tissues. VEGF-B is particularly abundant in heart and skeletal muscle and is co-expressed with VEGF in these and other tissues. In transfected cells, VEGF-B forms cell surface associated, disulfide-linked homodimers and heterodimers with VEGF when coexpressed.

EXAMPLE 1

Partial cDNA Clone with Two Reading Frames

A partial cDNA clone encoding murine VEGF-B was identified as follows. A cDNA library (E 14.5) derived from poly A+ mRNA isolated from 14.5 day old mouse embryos [Chevray P. and Nathans D., "Protein interaction cloning in yeast: Identification of mammalian proteins that react with the leucine zipper of Jun," *Proc. Natl. Acad. Sci. USA*, 89:5789–93 (1992)] was screened for cellular proteins which potentially might interact with cellular retinoic acid-binding protein type 1 (CRABP-I) using a yeast two-hybrid interaction trap screening technique as described by Gyuris J., Golemis E., Chertkov H. and Brent R., "Cdil, a Human G1 and S Phase Protein Phosphatase That Associates with Cdk2," *Cell*, 75:791–803 (1993). This screening technique involves a fusion protein that contains a binding domain and that is known to be transcriptionally inert (the "bait"); reporter genes that have no basal transcription and that are bound by the bait; and an expression library which encodes proteins expressed as chimeras and whose amino termini contain an activation domain and other useful moieties (the "prey"). The screened library was a plasmid library in the yeast expression vector pPC67 obtained from Dr. Pierre Chevray of the Johns Hopkins University, School of Medicine, 725 North Wolfe St., Baltimore, Md. 21205. A positive cDNA clone (pcif-2) was recovered from the screening. The positive clone was sequenced using well known, conventional techniques and found to encode a protein highly homologous to VEGF and the other members of the PDGF family of growth factors. The 890 base pair SalI-NotI insert in the plasmid pPC67 was cloned into pBluescript and fully sequenced using T7 and T3 vector primers together with internal primers. The plasmid pBluescript is commercially available from Stratagene Inc., LaJolla, Calif. The cDNA insert was found to be 886 base pairs long and to encode two polypeptides in different reading frames which were homologous to the N-terminal end and the C-terminal end, respectively, of VEGF. This novel growth factor is referred to hereinafter as VEGF-B. The clone is partial and lacks several amino acids in the amino terminal region and the entire signal sequence.

FIG. 1 shows the nucleotide sequence (SEQ ID NO:1) of this partial cDNA clone of VEGF-B and the amino acid sequence (SEQ ID NO:2) encoded in the first reading frame thereof. The DNA sequence of FIG. 1 was obtained by conventional sequencing of a clone (pcif-2) in the yeast expression vector pPC67. The clone comprised 886 base pairs and encoded a part of murine VEGF-B.

The isolated cDNA sequence will hybridize with the mammalian genomic DNA, e.g. either murine or human, which contains the VEGF-B gene. In addition to the coding sequence, the genomic DNA will contain one or more promoter sequence(s) which give and direct expression of VEGF-B in one or more specific tissues. Thus the coding sequence of VEGF-B may be linked to a muscular specific promoter which is specific to a certain type or types of tissue.

The nucleotide sequence is translated in two different reading frames into two different amino acid sequences. There is a stop codon (TGA) within the coding sequence at base pairs 309–311. Thus, VEGF-B comes in several splicing variants. The 5' end of the cloned cDNA sequence encodes an 102 amino acid long protein with significant homology to the N-terminal domains of VEGF, PlGF and PDGF A and B. In particular, a number of cysteine residues are perfectly conserved within this group of proteins. In addition to the nucleotide sequence (SEQ ID NO:1), FIG. 1 further depicts the deduced amino acid sequence (SEQ ID NO:2) of this first protein.

Translation of the C-terminal end of the cDNA (base pairs 308–475) in a different reading frame results in a protein which is highly homologous to the C-terminal part of VEGF$_{165}$, VEGF$_{189}$ and VEGF$_{206}$. FIG. 2 again shows the nucleotide sequence (SEQ ID NO:1) of FIG. 1, but this time includes the deduced amino acid sequece (SEQ ID NO:3) of the second protein, which is encoded in the second reading frame and is 54 amino acids long. It thus appears that the VEGF-B gene encodes different proteins using alternative splicing of the primary transcript. The last part of the clone, encoding the second peptide might be expressed as a functional protein in other spliced variants of VEGF-B.

The aforedescribed proteins may exist in combined association with an additional N-terminal sequence of approximately five (5) to ten (10) amino acids, as well as a further leader sequence of approximately twenty-one (21) to twenty-eight (28) amino acids. Inasmuch such combined amino acid sequences exhibit the property of promoting the proliferation of endothelial cells and the DNA sequences which code for such combined peptide sequences will hybridize under stringent conditions with the DNA sequence of FIGS. 1 and 2, such amino acid sequences and the DNA which codes for them are expressly contemplated to be within the scope of the present invention.

EXAMPLE 2

Cloning of Full Length cDNA's for Mouse VEGF-B

Using the approximately 0.9 kb Sal-I/Not-I cDNA insert of the previously identified cDNA clone of Example 1 as a probe, an adult mouse heart lambda ZAP-II cDNA library obtained from Stratagene Inc., of La Jolla, Calif. was screened using standard techniques. The library was titrated and plated as recommended and filters were prepared. Following prehybridization at 42° C. in 50% formamide, 5× SSPE, 5× Denharts solution, 1% SDS and 100 ug of salmon sperm DNA/ml, the filters were hybridized at the same temperature and in the same solution containing the denatured radiolabelled probe using 10$^6$ cpm/ml of hybridization solution. The probe was labelled using a random priming kit (Amersham). After 16 hours the filters were washed in 2× SSC containing 0.5% SDS for 2×30 mins at 52° C. The filters were exposed overnight using intensifying screens at −70° C. Positive clones were rescreened two times until all plaques on a plate were positive. The inserts from several positive clones were subcloned into the plasmid pbluescript SK+ by in vivo excision as recommended by the supplier.

Several clones were mapped by restriction enzyme analysis and were found to fall into two distinct groups characterized by the length of a Spe1/BamH1 restriction fragment. The first of these groups comprised three of the restriction mapped clones which each had a 240 bp Spe1/BamH1 restriction fragment. The other group comprised a clone which had a 340 bp Spe1/BamH1 fragment. Analysis of this fragment is described in Example 5.

The three clones which exhibited the 240 bp Spe1/BamH1 restriction fragment were fully or partially sequenced (Sequenase 2.0, U.S. Biochemicals), and the characteristics of the clones are summarized as follows:

Nucleotide sequence analyses revealed that two of the cDNA clones were substantially identical, although they differed in length, and one has a mutation. One of the clones was full length and contained an open reading frame encoding 188 amino acid residues in which the first 21 amino acids are a clevable signal sequence. The other of the two substantially identical clones terminated at the G of the start initiation codon. It could be inferred by sequence analysis of additional clones that the sequence preceeding the G reads ACCAT. Both of the clones were found to have the same coding region nucleotide sequence, which is depicted in FIG. 3 (SEQ ID NO:4). The deduced amino acid sequence of the open reading frame of the coding region of both of these two cDNA clones is shown in FIG. 4 (SEQ ID NO:5). The resulting protein encoded by this sequence is referred to hereinafter as VEGF-B$_{167}$. In each of the protein names used herein, the subscript number refers to the number of amino acids in the mature protein without the signal sequence.

As would be expected, a comparison of the amino acid sequence encoded by these two clones with the partial amino acid sequence deduced from cDNA clone of Example 1 showed a striking similarity. However, the two open reading frames in the clone of Example 1, each of which encoded an amino acid sequence homologous to a different portion of VEGF, are both present in the same reading frame in each of these two clones according to Example 2. The frame shift in the clone of Example 1 is caused by an insertion of two extra adenine units which displace the C-terminal part of the clone of Example 1 out of frame. The reason for this is not presently understood, but may be due to a cloning artifact.

The coding part of the third clone had a nucleotide sequence identical to those of the preceding two clones except for a 21 bp insertion. FIG. 5 shows the nucleotide sequence of this third clone (SEQ ID NO:6). To facilitate identification, the 21 extra bases are underlined in the Figure. This insertion gives rise to 7 additional amino acid residues in the mature protein. Thus the resulting protein encoded by this longer cDNA is termed VEGF-B$_{174}$. The amino acid sequence of the protein encoded by the cDNA of FIG. 5 is depicted in FIG. 6 (SEQ ID NO:7). The seven additional amino acids also are underlined in the figure for ease of identification. The additional amino acids are inserted into the sequence in a splice site, and sequencing of mouse genomic DNA clones indicates that these additional amino acids are the result of true alternative splicing. Furthermore, based on what is known about the receptor binding site locations of PDGF, the insertion occurs in a position in the protein which is probably part of a receptor binding site. The insertion is thus likely to affect receptor binding and could be of functional importance in influencing antagonist and/or different receptor specificity.

EXAMPLE 3

Hybrid cDNA Clone

As previously pointed out this original cDNA clone of Example 1 was not full length and may contain an artifact. However, if the extreme 5' nucleotide sequence of the clones which encode VFGF-B$_{167}$ and/or VEGF-B$_{174}$ is added, the open reading frame encodes a protein of 133 amino acids, yielding a mature protein which is 112 amino acids long and hence is named VEGF-B$_{112}$. The hybrid cDNA sequence encoding VEGF-B$_{112}$ is shown in FIG. 7, and the amino acid sequence of the corresponding protein is illustrated in FIG. 8.

FIG. 9 shows a multiple amino acid sequence alignment for comparison purposes of the 167 amino acid variant of mouse Vascular Endothelial Growth Factor B (mVEGF-B$_{167}$), mouse Vascular Endothelial Growth Factor (mVEGF$_{164}$), human Placenta Growth Factor (hPlGF), mouse Platelet Derived Growth Factor A (mPDGF A), and mouse Platelet Derived Growth Factor B (mPDGF B). Amino acid residues identical to mouse VEGF-B$_{167}$ are boxed. The homologous relationship of the sequences is apparent, and the figure clearly demonstrates the conserved structure of the growth factors belonging to the PDGF/ VEGF family of growth factors, and that VEGF-B is a structural homolog of the other growth factors of this group. Pairwise comparisons of the amino acid sequences show that mouse VEGF-B is approximately 43% identical to mouse $VEGF_{164}$, approximately 30% identical to human PlGF, and approximately 20% identical to mouse PDGF A and B. The conserved cysteine residues are particularly noteworthy. It can be seen that the first eight cysteine residues in the N-terminal domains (i.e. the PDGF-like domains) of the five growth factors are shared by all members of this family, and it is thus evident that the eight cysteine residues, which are involved in intramolecular and intermolecular disulfide bonding, are invariant among these growth factors. Furthermore, the C-terminal domains of mouse $VEGF-B_{167}$ and $VEGF_{164}$ also display a significant similarity with eight additional conserved cysteine residues and several stretches of basic amino acids.

EXAMPLE 4

Cloning of Human VEGF-B cDNA $10^6$ λ-clones of human fibrosarcoma cDNA library HT1080 in λgt11 (Clontech) were screened with the 0.9 kb insert of the mouse VEGF-B clone pcif 2 according to standard procedures. Among several positive clones, one, termed H.1 was analyzed more carefully and its nucleotide sequence was determined. The nucleotide sequence indicated that a 207 amino acid isoform of human VEGF-B was encoded. Analysis of this isoform is described subsequently in Example 6. Based on the H.1 sequence two oligonucleotides were designed that would amplify the whole coding region of putative human cDNA corresponding to mouse $VEGF-B_{167}$ form.

5'-CACCATGAGCCCTCTGCTCC-3' (forward) (SEQ ID NO:17)

5'-GCCATGTGTCACCTTCGCAG-3' (reverse) (SEQ ID NO:18)

These oligonucleotides were used to amplify by polymerase chain reaction (PCR) the whole coding region of human VEGF-B from oligo-dT primed human erythroleukemia cell (HEL) RNA. The amplified product was cloned into the pCR II-vector of TA cloning kit (Invitrogen) and sequenced using standard techniques. The nucleotide sequence of the human VEGF-B cDNA clone is shown in FIG. 10 (SEQ ID NO:10) , and the deduced amino acid sequence of human VEGF-$B_{167}$ is shown in FIG. 11 (SEQ ID NO:11).

The full length mouse cDNA clone of Example 2 and the full length human cDNA clone of Example 4 each encode a polypeptide of 188 amino acids containing an N-terminal hydrophobic putative signal sequence. In analogy with VEGF, the signal peptidase cleavage site is believed to be located between Ala 21 and Pro 22. The putative cleavage site of the signal peptidase is indicated in FIG. 16 by an arrow. Accordingly, the processed VEGF-B polypeptides of these two clones each contain 167 amino acids.

EXAMPLE 5

The clone which exhibited the 340 bp Spe1/BamH1 fragment isolated in Example 2 was analyzed, and the major portion was found to be identical to the first two clones of Example 2 which exhibited the 240 bp Spe1/BamH1 fragment. The difference is due to the presence of an insertion in the C-terminal part of the sequence.

This 340 bp Spe1/BamH1 DNA fragement encodes a further isoform of mouse VEGF-B containing 207 amino acids. The coding portion of the DNA encoding this protein is illustrated in FIG. 12, and the translated amino acid sequence is illustrated in FIG. 13. After cleavage of the 21 amino acid leader sequence, the mature protein contains 186 amino acids and is referred to as $mVEGF-B_{186}$. This isoform is clearly a result of alternative DNA splicing as described below with reference to FIG. 17.

EXAMPLE 6

The H.1 clone isolated as described in Example 4 was found to encode a 207 amino acid isoform of human VEGF-B. The coding portion of the DNA encoding this protein is illustrated in FIG. 14 and the translated amino acid sequence is illustrated in FIG. 15. Again, this isoform, which is designated $hVEGF-B_{186}$, appears to be a product of alternative splicing.

FIG. 16 shows the aligned amino acid sequences of mouse and human $VEGF-B_{167}$ and $VEGF-B_{186}$ in one-letter code. Identical residues are enclosed in boxes, while amino acid residues which differ between mouse and human $VEGF-B_{167}$ and $VEGF-BE_{186}$ isoforms are outside the boxes. Mouse and human VEGF-B display approximately 88% amino acid sequence identity and are highly basic, especially in their C-terminal regions. Both polypeptides lack the consensus sequence for N-linked glycosylation (N-X-T/S). The arrow indicates the putative cleavage site for the signal peptidase. Excluding the signal sequences, the mouse and human $VEGF-B_{167}$ amino acid sequences are highly homologous with only 20 replacements out the the 167 residues. The replacements are clustered in the N-terminus, in two regions around amino acids 60 and 145. All cysteine residues in both $VEGF-B_{167}$ proteins are invariant, but the eight cysteine residues in the C-terminal end of $VEGF-B_{167}$ are not conserved in the $VEGF-B_{186}$ isoforms. It is notable that the mouse and human sequences in the region between residues 66 and 129 are identical apart from one evolutionarily conserved replacement (Q105R). This is of importance since the receptor binding domains are found within this portion of the protein (compared to PDGF structure). From this it can be concluded that it is likely that mouse and human VEGF-B will exhibit cross-reactive binding on the receptor level and thus display identical or similar biological activities.

FIG. 17 is a schematic representation of the structure of mouse and human genes for VEGF-B. Each of the genes contains seven exons. Exon 6 contains an alternative splice acceptor site which enables the gene to produce two different transcripts for VEGF-B. $VEGF-B_{167}$ uses exons 1–5, the last part of exon 6, and exon 7 (TGA). $VEGF-B_{186}$ uses exons 1 through 5, the first part of exon 6, and terminates in the last part of exon 6 (TAG). Exon 7 is not translated in $VEGF-B_{186}$ since the insertion of the first part of exon 6 introduces a frame shift and gives rise to a stop codon in the last part of exon 6.

Figure 18:
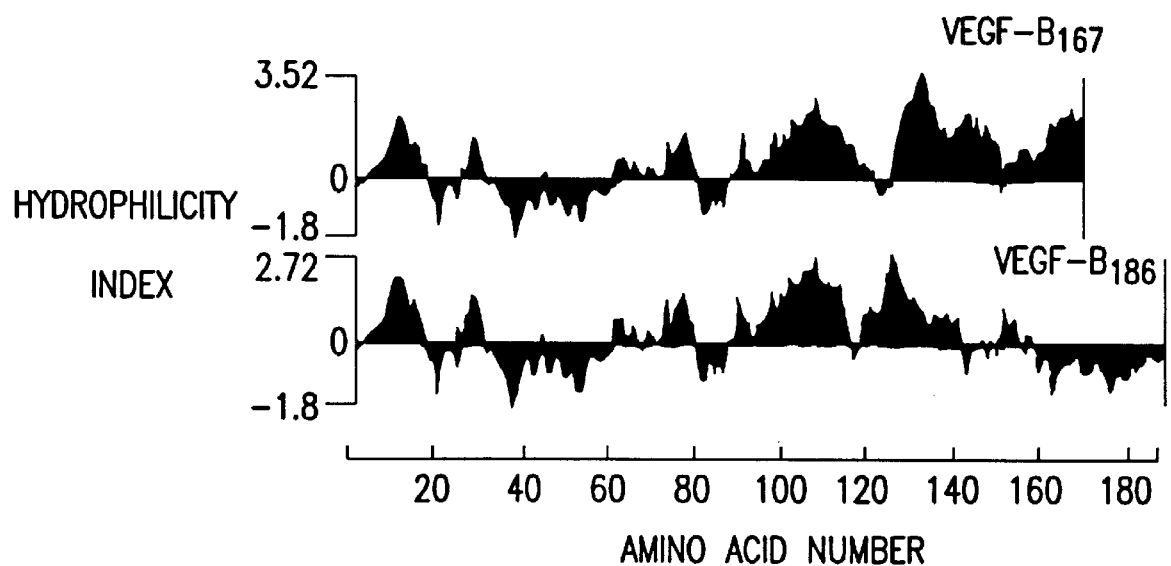
FIG. 18 shows a hydrophilicity analysis of murine VEGF-$B_{167}$ and VEGF-$B_{186}$ isoforms.

FIG. 18 shows a comparative hydrophilicity analysis of murine $VEGF-B_{167}$ and $VEGF-B_{186}$. As would be expected, the pattern of hydrophilicity/hydrophobicity is essentially identical from amino acid 1 through amino acid 115. After amino acid 115, the hydrophilicity/hydrophobicity patterns diverge because of the frame shift introduced by the first part of exon 6. Thus, $VEGF-B_{167}$ and $VEGF-B_{186}$ can be expected to exhibit both similar and dissimilar activities.

Figure 19:
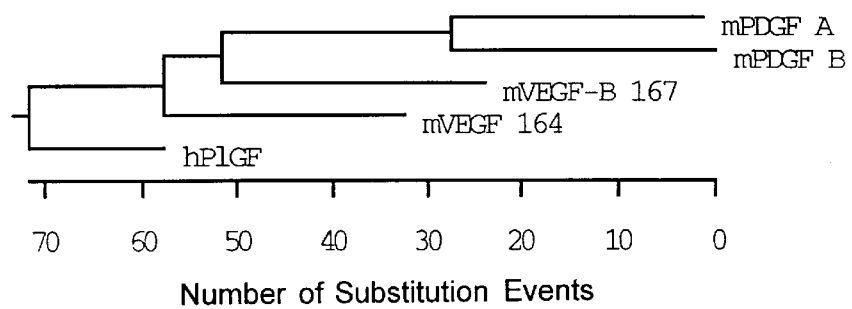
FIG. 19 shows a phylogenetic analysis of the VEGF/PDGF family of growth factors.

FIG. 19 is a dendrogram showing the phylogenetic relationship of the amino acid sequences of five members of the VEGF/PDGF family of growth factors. The number of replacements or substitutions decreases from the left to the right of the chart. It can be seen that VEGF-B lies between VEGF and the platelet derived growth factor (PDGF) group.

The multiple amino acid sequence alignments of FIGS. 9 and 16 and the phylogenetic analysis of FIG. 19 were carried out accoring to Hein, *Method in Enzymology*, Vol. 183, pp. 626–45, Academic Press Inc., San Diego (1990) using the PAM 250 distance table.

EXAMPLE 7

Antibody Production

Antipeptide antiserum to human VEGF-B was generated by immunizing rabbits with a branched 23-mer oligopeptide comprising the following N-terminal region amino acid residue sequence (SEQ ID NO:19):

S-Q-P-D-A-P-G-H-Q-R-K-V-V-S-W-I-D-V-Y-T-R-A-T.

The branched 23-mer oligo peptide was synthesized according to Tam, "Synthetic peptide vaccine design: synthesis and properties of a high-density multiple antigenic peptide system", *Proc. Natl. Acad. Sci. USA*, Vol. 85, pages 5409–413 (1988). In the first immunization, rabbits were subcutaneously injected with 500 μg of the branched peptide emulsified in Complete Freunds Adjuvant. In the subsequent boosters, 200 μg of the antigen emulsified in Incomplete Freunds Adjuvant was injected. Antisera were collected after the second and third boosters by conventional techniques.

EXAMPLE 8

Biochemical Properties of VEGF-B$_{167}$, Homodimerization, and Heterodimerization with VEGF The biochemical properties of human VEGF-B$_{167}$ were examined in transfected human embryonic kidney 293EBNA cells (Invitrogen Corp.). cDNA inserts encoding human VEGF-B$_{167}$ and human VEGF$_{165}$ [see Keck et al., *Science*, Vol. 246, pages 1309–312 (1989)] were individually cloned into the pREP7 expression vector (Invitrogen Inc.). Human embryo kidney 293EBNA cells (expressing Epstein-Barr virus nuclear antigen-1) were transfected by transient transfection with the respective expression plasmids using calcium phosphate precipitation, and the cells were incubated for 48 hrs. As a control, cells also were transfected with an expression vector containing the VEGF-B$_{167}$ cDNA in reverse orientation. Monolayers of cells were incubated in methionine-free and cysteine-free medium for 30 minutes followed by labeling with 100 μCi/ml [$^{35}$S] methionine and [$^{35}$S]cysteine (Promix, Amersham Inc.) in the same medium for 2 hours. The labeling medium was replaced with normal medium without serum, and labelled proteins were chased for 6 hours. Heparin was included during the chase when indicated (100 μg/ml). Media were collected after the chase period, and cells were solubilized in 10 mM Tris pH 7.5, 50 mM NaCl, 0.5% sodium deoxycholate, 0.5% Nonidet P-40, 0.16 SDS and 0.1 U/ml aprotinin.

VEGF-B$_{167}$ was expressed in the cells transfected with the plasmids containing the VEGF-B$_{167}$ DNA. Aliquots of the culture supernatants from cells treated or untreated with heparin and detergent solubilized cell lysates were subjected to immunoprecipitation with the specific antipeptide antiserum to VEGF-B described in Example 7 and analyzed by SDS-PAGE under reducing conditions unless otherwise indicated. The data show that VEGF-B$_{167}$ homodimers and VEGF-B$_{167}$–VEGF$_{165}$ heterodimers are released from cells by heparin. By heparin treatment (1–100 μg/ml) or 1.2M NaCl, VEGF-B$_{167}$ was released from cells and found in the supernatant. If cells were not treated with heparin, VEGF-B$_{167}$ remained cell-associated and was not released into the culture media. Under the same conditions, VEGF$_{165}$ homodimers are secreted from the cells and found in the culture supernatants without heparin treatment.

Under reducing conditions, human VEGF-B$_{167}$ migrated with a Mr of 21 kDa. Analysis of culture supernatants under non-reducing conditions showed that VEGF-B$_{167}$ migrated as an Mr 42 kDa species indicating a dimeric structure. These results suggest that VEGF-B$_{167}$ forms disulfide-linked dimers associated with the cell surface, probably through ionic interactions with extracellular heparan sulfate proteoglycans. The association is likely to be mediated by the C-terminal basic domain, as observed for the longer splice variants of VEGF.

Since VEGF has been shown to form heterodimers with PlGF, it was decided to test whether VEGF$_{165}$ could also form heterodimers with VEGF-B$_{167}$. For this purpose 293EBNA cells were co-transfected with expression vectors encoding both human VEGF$_{165}$ and human VEGF-B$_{167}$, and VEGF-B$_{167}$ was expressed in combination with VEGF$_{165}$. Metabolically labelled proteins were chased in the presence of heparin and immunoprecipitations were carried out with antisera to either VEGF-B$_{167}$ or VEGF$_{165}$. The antiserum to human VEGF was from R&D Systems. Under non-reducing conditions the VEGF-B$_{167}$–VEGF$_{165}$ heterodimers migrated as Mr 42–46 kDa species. The results show that VEGF-B can form disulfide linked heterodimers with VEGF, which, in the absence of heparin, remain cell-associated. Since homodimers of VEGF$_{165}$ are efficiently secreted into the media, VEGF-B appears to determine the secretion of the heterodimer.

VEGF-B is synthesized normally in the endoplasmic reticulum of the source cell for subsequent export. Recombinant VEGF-B may be produced by inserting a DNA sequence encoding the VEGF-B protein together with a suitable operatively linked promoter and control sequences into a suitable vector, such as the well known plasmid pBR322 or a derivative thereof, transforming or transfecting a suitable host cell, such as *E. coli* or a Cos cell, with the resulting vector or other systems well known in the art, screening the resulting transformants or transfectants for VEGF-B expression, and then culturing cell lines or bacterial cell strains which are positive for the expression of VEGF-B. Either a eukaryotic vector or a prokaryotic vector may be used, depending on the type of cell which is to be transfected or transformed therewith. A particularly preferred system for production of recombinant VEGF-B is the baculovirus—insect cell system, which has proved capable of producing excellent yields of recombinant protein.

EXAMPLE 9

VEGF-B Expression Using the Baculovirus System
9.1 VEGF-B with its own signal peptide.
a) Cloning and Transfection.

The complete human VEGF-B$_{167}$ gene was inserted into a commercially available plasmid pCRII (Invitrogen Corp.). The HindIII-XbaI fragment from the resulting plasmid pCRII-VEGF-B$_{167}$, which encodes the whole open reading frame of VEGF-B$_{167}$ then was cloned into pFASTBAC1, and both the 3'- and 5'-junctions were sequenced. Bacmid-DNA was prepared according to the manufacturers instructions for the "Bac-To-Bac™ Baculovirus Expression System" (Life Technologies Inc.) and lipofected to Sf900II-adapted Sf9 cells (obtained from Dr. Christian Oker-Blom). Sf9 cells are from the American Type Culture Collection Cell Repository Line Bank, Rockville Md. (ATCC CRL- 1711). The transfected cells were then cultured on standard TMN-FH medium in 25 cm² culture dishes.

b) Assay for protein expression.

About 72 hours after transfection, the cells were lysed and 1 ml of culture supernatant and the cell lysate were assayed for expressed VEGF-B by immunoprecipitation as described in Example 8 and Western blotting. Lysates from three out of four independently transfected cell cultures were found positive for VEGF-B, although the intensity of the signal in the Western blot varied. The expressed VEGF-B polypeptide in each case was found to correspond in size to the protein expressed in mammalian cells in Example 8.

The viral stock from the cells that gave the strongest signal in Western blotting was amplified two rounds by infecting cells and collecting new virus from the medium. The resulting supernatant was analyzed. Uninfected cells were also analyzed as a negative control. Time course analysis showed that cells harvested between 48 and 72 hours after infection contained the greatest amount of VEGF-B. After 96 hours post infection, as a result of virus-induced cell lysis, VEGF-B could also be detected in the culture supernatant by immunoprecipitation and Western blotting. Recombinant VEGF-B could be precipitated from the lysate between 20% and 40% $(NH_4)_2SO_4$.

9.2 VEGF-B with the Melittin signal peptide (pVTBac).

a) Cloning and transfection.

A polymerase chain reaction (PCR) fragment from nucleotide position 68 to 141 was used to introduce a BamHI restriction site immediately after the signal cleavage site in the plasmid pCRII-VEGF-$B_{167}$ from Example 10.1. The BamHI fragment from this modified pCRII-VEGF-$B_{167}$ construct was cloned into BamHI opened pVTBac [Tessier et al., "Enhanced secretion from insect cells of a foreign protein fused to the honeybee mellitin signal peptide", *Gene*, Vol. 98, page 177 (1991)]. Both 3'- and 5'-junction were sequenced. Sf9 cells were cotransfected with the aforedescribed pVTBac vector which contained the human VGEF-$B_{167}$ gene, and with linearized baculovirus DNA (Insectin™, Invitrogen Corp.). The transfected cells then were cultured in TMN-FH medium.

b) Assay for protein expression.

Forty-eight hours after transfection, the supernatant was collected and subjected to primary screening by immunoprecipitation. Four positive plaques were isolated.

EXAMPLE 10

Stimulation of Cell Proliferation

The ability of VEGF-$B_{167}$ to stimulate endothelial cell proliferation was established through analysis of [³H] thymidine incorporation in human umbilical vein endothelial cells (HUVEC) and in bovine capillary endothelial (BCE) cells.

293EBNA cells were transfected with expression vectors for VEGF-$B_{167}$, VEGF$_{165}$ or empty vector (mock) in the presence of 1 μg/ml heparin. Conditioned media from these cells were diluted in respective media, applied to human umbilical vein endothelial cells (HUVEC) and to bovine capillary endothelial (BCE) cells and incorporation of [³H] thymidine was measured. As a positive control recombinant bFGF was added to BCE cells.

To elaborate, conditioned media containing human VEGF-B and human VEGF$_{165}$ were collected from 293EBNA cells transfected with the appropriate expression vectors or with empty vector (mock) in the presence of heparin (1 μg/ml) 48 hours posttransfection. Second passage HUVEC were plated into 96-well plates (4×10³ cells/well) in M-199 medium supplemented with 10% fetal bovine serum and incubated for 24 hours. Conditioned media were diluted with the growth medium and cells were stimulated for 48 hours. Fresh conditioned media containing 10 μCi/ml of [³H]thymidine (Amersham Inc.) were added to the cells and stimulations were continued for another 48 hours. Cells were washed with PBS and trypsinized and incorporated radioactivity was determined by liquid scintillation counting. BCE cells were seeded into 24-well plates and grown until confluence in minimal essential medium (MEM) supplemented with 10% fetal calf serum. Cells were starved in MEM supplemented with 3% fetal calf serum for 72 hours, after which conditioned media diluted into serum-free medium were added to the cells and the cells were stimulated for 24 hours. [³H]Thymidine was included during the last 4 hours of the stimulation (1 μCi/ml). Stimulations with bFGF were carried out as above using 6 ng/ml of recombinant bFGF (Synergen Inc.). Cells were washed with PBS, lysed with NaOH, and incorporated radioactivity was determined by liquid scintillation counting.

Figure 20:
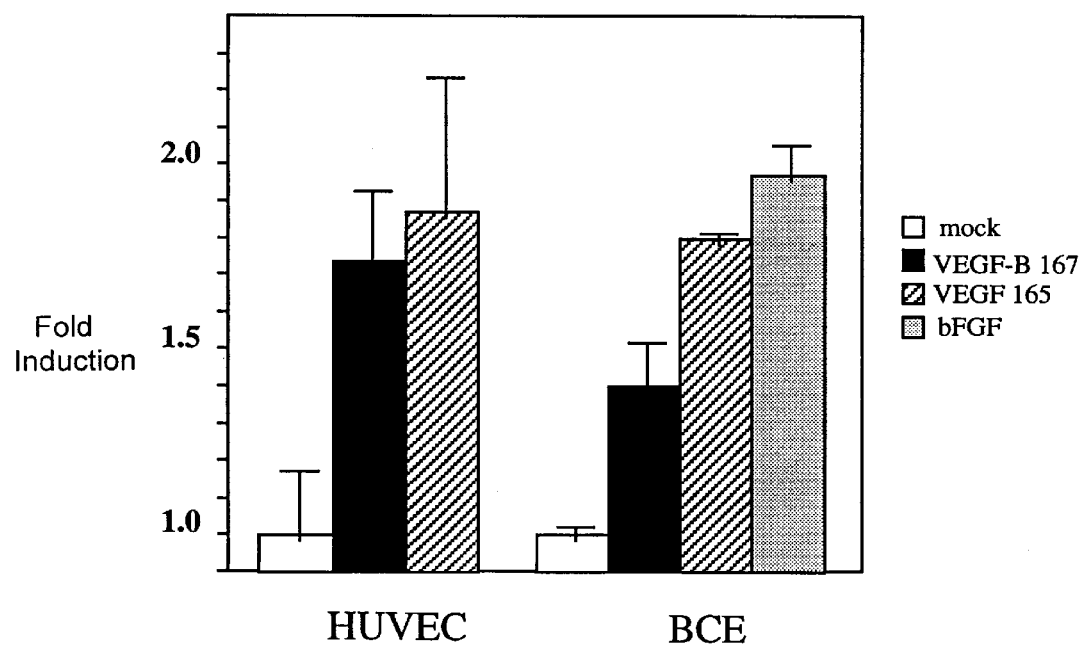
FIG. 20 is a graph showing the induction of [$^3$H] thymidine incorporation by VEGF-B, VEGF and bFGF for human umbilical vein endothelial cells (HUVEC) and bovine capillary endothelial (BCE) cells.

FIG. 20 is a bar graph showing fold of induction of [³H]thymidine incorporation by VEGF-$B_{167}$ in human umbilical vein endothelial cells (HUVEC) and in bovine capillary endothelial (BCE) cells, as compared to basal activity induced by conditioned medium from the mock transfected cells. For comparison purposes, the induction by VEGF$_{165}$ and by bFGF are also shown. The bars show the mean ± standard deviation of parallel samples. Similar results were obtained in several other independent experiments. The test results clearly show that VEGF-B induced [³H]thymidine incorporation in both HUVEC and BCE cells and stimulated proliferation of endothelial cells in vitro, thereby demonstrating that VEGF-B is an endothelial growth factor.

The foregoing results indicate that that VEGF-B is a novel growth factor for endothelial cells which plays a role in vascularization, in particular of muscle. The cell-association of VEGF-B may have several implications for regulation of vascularization and endothelial cell growth. In developing embryos and in contractile tissues, cell-associated VEGF-B may provide spatial cues to outgrowing endothelial cells during establishment and maintenance of the vascular tree. It could also, through its cell-association, support the regeneration of damaged endothelium in adult vessels. The ability of VEGF-B to modulate the secretion of VEGF by heterodimer formation suggests an indirect role of VEGF-B in VEGF signalling. The formation of multiple heterodimeric complexes of these growth factors could provide a basis for a diverse array of regulatory signals for endothelial cells.

VEGF-B can be used as a growth factor for populations of endothelial cells in vitro. VEGF-B may be used to promote desirable angiogenesis, i.e. the formation of new blood vessels and capillaries. For example, it may be useful in promoting the development of the corpus luteum and endometrium as an aid to initiating and/or maintaining pregnancy. It would also be useful in bone repair by virtue of its action on endothelial cells. Administration of VEGF-B may also be useful in supporting embryogenesis, as well as somatic growth and vascular development and differentiation. Topical application of VEGF-B to wounds may be useful in promoting wound healing, and oral administration of VEGF-B may be useful to accelerate the healing of gastric and/or duodenal ulcers. The ability of VEGF-B to modulate the secretion of VEGF by heterodimer formation could provide a therapeutic role for VEGF-B in diseases where VEGF agonists would be useful.

VEGF-B may exert proliferative effects on mesodermal cells either directly or via improvements in the blood supply.

Tumor assays for VEGF-B may be useful as indicators of metastatic risk. Assays of VEGF-B in body fluids or the tumor itself by histochemistry may be useful as a tumor prognostic factor. Furthermore, because tumor growth requires angiogenesis, administration of VEGF-B may also be useful in promoting tumor growth in laboratory animals in order to test anti-tumorigenic drugs. VEGF-B may also be useful to increase the microvascularity of hypoxic areas of tumors and make them more sensitive to radiation, radiation sensitizing drugs, etc.

The angiogenic action of VEGF-B may be useful in treating ischemic conditions. VEGF-B or agonists could be used to stimulate the development of collateral circulation in cases of arterial and/or venous obstruction, e.g. myocardial infarcts, ischaemic limbs, deep venous thrombisis, and/or postpartum vascular problems.

A VEGF-B/VEGF-B receptor system may be used as an assay system to detect small molecules as agonists/antagonists for development as new drugs. Examples of small molecules which could be detected include, but are not limited to, organic chemicals, peptides, and RNA molecules.

Pharmaceutical compositions may be produced by admixing a pharmaceutically effective amount of VEGF-B protein with one or more suitable carriers or adjuvants such as water, mineral oil, polyethylene glycol, starch, talcum, lactose, thickeners, stabilizers, suspending agents, etc. Such compositions may be in the form of solutions, suspensions, tablets, capsules, creams, salves, ointments, or other conventional forms.

As demonstrated in Example 7, VEGF-B protein also can be used to produce antibodies. In general, conventional antibody production techniques may be used to produce VEGF-B antibodies. For example, specific monoclonal antibodies may be produced via immunization of fusion proteins obtained by recombinant DNA expression.

Labelled monoclonal antibodies, in particular, should be useful in screening for conditions associated with abnormal levels of VEGF-B in the body. For example, assays of VEGF-B levels in blood or urine may be useful as a tumor marker. These monoclonal antibodies to VEGF-B also may be useful in inhibiting angiogenesis associated with high levels of VEGF-B in the body, e.g. in rapidly proliferating, angiogenesis-dependent tumors in mammals, and thereby may retard the growth of such tumors. Treatment may be effected, e.g., by twice weekly intraperitoneal injection of 10 to 500 $\mu$g, preferably 50–100 $\mu$g of monoclonal antibody. For the therapy of humans, chiaserization or humanization of such monoclonal antibodies is to be preferred.

VEGF-B antagonists such as antibodies may be useful to inhibit new blood vessels in diabetic retinopathy, psoriasis, arthopathies and/or vascular tumors such as haemangiomas.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An isolated nucleic acid which codes for a protein which comprises the amino acid sequence:

Pro-Xaa-Cys-Val-Xaa-Xaa-Xaa-Arg-Cys-Xaa-Gly-Cys-Cys (SEQ ID NO:16) and has the property of promoting proliferation of endothelial cells or mesodermal cells, said nucleic acid being selected from the group consisting of the DNA of SEQ ID NO:1, the DNA of SEQ ID NO:4, the DNA of SEQ ID NO:6, the DNA of SEQ ID NO:8, the DNA of SEQ ID NO:10, the DNA of SEQ ID NO:12, the DNA of SEQ ID NO:14, and nucleic acids which hybridize at 42° C. in 50% formamide, 5×0.75M sodium chloride and 0.075M sodium citrate pH 7.0 or 5× buffer composed of 0.9M sodium chloride, 0.05M sodium phosphate, pH 7.7 and 0.005M ethylene diamine tetraacetic acid, 1% to 2% sodium dodecyl sulfate, 5 to 10× Denhardt's solution and 100 µg/ml of salmon sperm DNA with at least one of the foregoing sequences.

2. An isolated nucleic acid according to claim 1, wherein said nucleic acid is a cDNA.

3. An isolated nucleic acid according to claim 1, comprising the sequence set forth as SEQ ID NO:1.

4. An isolated nucleic acid according to claim 1, wherein said nucleic acid is a mammalian DNA.

5. An isolated nucleic acid according to claim 4, wherein said nucleic acid is a murine DNA.

6. An isolated nucleic acid according to claim 4, wherein said nucleic acid is a human DNA.

7. An isolated nucleic acid according to claim 1, wherein said nucleic acid codes for a protein which promotes proliferation of vascular endothelial cells.

8. An isolated nucleic acid according to claim 1, comprising the sequence set forth as SEQ ID NO:4.

9. An isolated nucleic acid according to claim 1, comprising the sequence set forth as SEQ ID NO:6.

10. An isolated nucleic acid according to claim 1, comprising the sequence set forth as SEQ ID NO:8.

11. An isolated nucleic acid according to claim 1, comprising the sequence set forth as SEQ ID NO:10.

12. An isolated nucleic acid according to claim 1, comprising the sequence set forth as SEQ ID NO:12.

13. An isolated nucleic acid according to claim 1, comprising the sequence set forth as SEQ ID NO:14.

14. A vector comprising a nucleic acid according to claim 1, which nucleic acid is operably linked with a promoter sequence.

15. A vector according to claim 14, wherein said vector is a eukaryotic vector.

16. A vector according to claim 14, wherein said vector is a prokaryotic vector.

17. A vector according to claim 14, wherein said vector is a plasmid.

18. A host cell transformed or transfected with a vector according to claim 14.

19. A host cell according to claim 18, wherein said host cell expresses a protein having the property of promoting proliferation of endothelial or mesodermal cells.

20. A transfected host cell according to claim 18, wherein said host cell is a eukaryotic cell.

21. A transfected host cell according to claim 18, wherein said host cell is a COS cell.

22. A transformed host cell according to claim 18, wherein said host cell is a prokaryotic cell.

23. A transformed host cell according to claim 18, wherein said host cell is a 293EBNA cell.

24. A transformed host cell according to claim 18, wherein said host cell is an insect cell.

25. A means for amplifying a vascular endothelial growth factor-B (VEGF-B) polynucleotide in a test sample, said means comprising a polymerase and at least one pair of primers complementary to a nucleic acid according to claim 1, for amplifying the VEGF-B polynucleotide by polymerase chain reaction in order to facilitate a sequence comparison of the VEGF-B polynucleotide with the nucleic acid according to claim 1.

26. A host cell transformed or transfected with a vector comprising a nucleic acid sequence according to claim 1, operatively linked to a promoter, such that said host cell expresses a VEGF-B protein.

27. A means for amplifying a VEGF-B polynucleotide in a test sample, said means comprising at least one pair of primers complementary to a nucleic acid according to claim 1.

28. A method of making a vector which expresses VEGF-B protein, said method comprising incorporating an isolated nucleic acid according to claim 1, into said vector in operatively linked relation with a promoter.

29. An isolated nucleic acid molecule which encodes a human VEGF-B molecule, wherein said isolated nucleic acid molecule hybridizes to at least one nucleic acid molecule selected from the group consisting of SEQ ID NO:1, SEQ ID NO:4, SEQ ID NO:6, SEQ ID NO:8 and SEQ ID NO:12, at 42° C. in 50% formamide, 5×0.75M sodium chloride and 0.075M sodium citrate pH 7.0 or 5× buffer composed of 0.9M sodium chloride, 0.05M sodium phosphate, pH 7.7 and 0.005M ethylene diamine tetraacetic acid, 1% to 2% sodium dodecyl sulfate, 5 to 10× Denhardt's solution and 100 µg/ml of salmon sperm DNA.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 886 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (vi) ORIGINAL SOURCE:
      (F) TISSUE TYPE: mouse embryo (vii) IMMEDIATE SOURCE:
      (B) CLONE: pcif2

(xi) SEQUENCE DESCRIPTION: SEQ ID NO:1:

```
CGGGACGCCC AGTGGTGCCA TGGATAGACG TTTATGCACG TGCCACATGC CAGCCCAGGG      60

AGGTGGTGGT GCCTCTGAGC ATGGAACTCA TGGGCAATGT GGTCAAACAA CTAGTGCCCA     120

GCTGTGTGAC TGTGCAGCGC TGTGGTGGCT GCTGCCCTGA CGATGGCCTG GAATGTGTGC     180

CCACTGGGCA ACACCAAGTC CGAATGCAGA TCCTCATGAT CCAGTACCCG AGCAGTCAGC     240

TGGGGGAGAT GTCCCTGGAA GAACACAGCC AATGTGAATG CAGACCAAAA AAAAAAGGA      300

GAGTGCTGTG AAGCCAGACA GCCCCAGGAT CCTCTGCCCG CCTTGCACCC AGCGCCGTCA     360

ACGCCCTGAC CCCCGGACCT GCCGCTGCCG CTGCAGACGC CGCCGCTTCC TCCATTGCCA     420
```

-continued

```
AGGGCGGGGC TTAGAGCTCA ACCCAGACAC CTGTAGGTGC CGGAAGCCGC GAAAGTGACA    480

AGCTGCTTTC CAGACTCCAC GGGCCCGGCT GCTTTTATGG CCCTGCTTCA CAGGGACGAA    540

GAGTGGAGCA CAGGCAAACC TCCTCAGTCT GGGAGGTCAC TGCCCCAGGA CCTGGACCTT    600

TTAGAGAGCT CTCTCGCCAT CTTTTATCTC CCAGAGCTGC CATCTAACAA TTGTCAAGGA    660

ACCTCATGTC TCACCTCAGG GGCCAGGGTA CTCTCTCACT TAACCACCCT GGTCAAGTGA    720

GCATCTTCTG GCTGGCTGTC TCCCCTCACT ATGAAAACCC CAAACTTCTA CCAATAACGG    780

GATTTGGGTT CTGTTATGAT AACTGTGACA CACACACACA CTCACACTCT GATAAAAGAG    840

AACTCTGATA AAGAGATGG AAGACACTAA AAAAAAAAAA AAAAAA                    886
```

(2) INFORMATION FOR SEQ ID NO:2:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: mouse embryo (xi) SEQUENCE DESCRIPTION: SEQ ID NO:2:

```
Gly Arg Pro Val Val Pro Trp Ile Asp Val Tyr Ala Arg Ala Thr Cys
1               5                  10                  15

Gln Pro Arg Glu Val Val Pro Leu Ser Met Glu Leu Met Gly Asn
            20                  25                  30

Val Val Lys Gln Leu Val Pro Ser Cys Val Thr Val Gln Arg Cys Gly
        35                  40                  45

Gly Cys Cys Pro Asp Asp Gly Leu Glu Cys Val Pro Thr Gly Gln His
    50                  55                  60

Gln Val Arg Met Gln Ile Leu Met Ile Gln Tyr Pro Ser Ser Gln Leu
65                  70                  75                  80

Gly Glu Met Ser Leu Glu Glu His Ser Gln Cys Glu Cys Arg Pro Lys
                85                  90                  95

Lys Lys Arg Arg Val Leu
            100
```

(2) INFORMATION FOR SEQ ID NO:3:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: mouse embryo (xi) SEQUENCE DESCRIPTION: SEQ ID NO:3:

```
Lys Pro Asp Ser Pro Arg Ile Leu Cys Pro Pro Cys Thr Gln Arg Arg
1               5                  10                  15

Gln Arg Pro Asp Pro Arg Thr Cys Arg Cys Arg Cys Arg Arg Arg Arg
            20                  25                  30

Phe Leu His Cys Gln Gly Arg Gly Leu Glu Leu Asn Pro Asp Thr Cys
```

```
              35                  40                  45
Arg Cys Arg Lys Pro Arg Lys
    50                  55
```

(2) INFORMATION FOR SEQ ID NO:4:

(i) SEQUENCE CHARACTERISTICS:
        (A) LENGTH: 565 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (F) TISSUE TYPE: adult mouse heart (xi) SEQUENCE DESCRIPTION: SEQ ID NO:4:

```
GAGCCCCCTG CTCCGTCGCC TGCTGCTTGT TGCACTGCTG CAGCTGGCTC GCACCCAGGC     60

CCCTGTGTCC CAGTTTGATG GCCCCAGCCA CCAGAAGAAA GTGGTGCCAT GGATAGACGT    120

TTATGCACGT GCCACATGCC AGCCCAGGGA GGTGGTGGTG CCTCTGAGCA TGGAACTCAT    180

GGGCAATGTG GTCAAACAAC TAGTGCCCAG CTGTGTGACT GTGCAGCGCT GTGGTGGCTG    240

CTGCCCTGAC GATGGCCTGG AATGTGTGCC CACTGGGCAA CACCAAGTCC GAATGCAGAT    300

CCTCATGATC CAGTACCCGA GCAGTCAGCT GGGGGAGATG TCCCTGGAAG AACACAGCCA    360

ATGTGAATGC AGACCAAAAA AAAAGGAGAG TGCTGTGAAG CCAGACAGCC CCAGGATCCT    420

CTGCCCGCCT TGCACCCAGC GCCGTCAACG CCCTGACCCC CGGACCTGCC GCTGCCGCTG    480

CAGACGCCGC CGCTTCCTCC ATTGCCAAGG GCGGGGCTTA GAGCTCAACC CAGACACCTG    540

TAGGTGCCGG AAGCCGCGAA AGTGA                                          565
```

(2) INFORMATION FOR SEQ ID NO:5:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: adult mouse heart (xi) SEQUENCE DESCRIPTION: SEQ ID NO:5:

```
Met Ser Pro Leu Leu Arg Arg Leu Leu Leu Val Ala Leu Leu Gln Leu
1               5                  10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
        35                  40                  45

Pro Arg Glu Val Val Val Pro Leu Ser Met Glu Leu Met Gly Asn Val
    50                  55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
```

```
            100                  105                    110
Glu Met Ser Leu Glu Glu His Ser Gln Cys Glu Cys Arg Pro Lys Lys
            115                  120                    125

Lys Glu Ser Ala Val Lys Pro Asp Ser Pro Arg Ile Leu Cys Pro Pro
        130                  135                    140

Cys Thr Gln Arg Arg Gln Arg Pro Asp Pro Thr Cys Arg Cys Arg
145                 150                    155                 160

Cys Arg Arg Arg Arg Phe Leu His Cys Gln Gly Arg Gly Leu Glu Leu
                165                  170                    175

Asn Pro Asp Thr Cys Arg Cys Arg Lys Pro Arg Lys
            180                  185

(2) INFORMATION FOR SEQ ID NO:6:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (F) TISSUE TYPE: adult mouse heart (xi) SEQUENCE DESCRIPTION: SEQ ID NO:6:

ACCATGAGCC CCCTGCTCCG TCGCCTGCTG CTTGTTGCAC TGCTGCAGCT GGCTCGCACC      60

CAGGCCCCTG TGTCCCAGTT TGATGGCCCC AGCCACCAGA AGAAAGTGGT GCCATGGATA     120

GACGTTTATG CACGTGCCAC ATGCCAGCCC AGGGAGGTGG TGGTGCCTCT GAGCATGGAA     180

CTCATGGGCA ATGTGGTCAA ACAACTAGTG CCCAGCTGTG TGACTGTGCA GCGCTGTGGT     240

GGCTGCTGCC CTGACGATGG CCTGGAATGT GTGCCCACTG GCAACACCA  AGTCCGAATG     300

CAGGTACCAG GGCCTATGGG TCAGATCCTC ATGATCCAGT ACCCGAGCAG TCAGCTGGGG     360

GAGATGTCCC TGGAAGAACA CAGCCAATGT GAATGCAGAC CAAAAAAAAA GGAGAGTGCT     420

GTGAAGCCAG ACAGCCCCAG GATCCTCTGC CCGCCTTGCA CCCAGCGCCG TCAACGCCCT     480

GACCCCCGGA CCTGCCGCTG CCGCTGCAGA CGCCGCCGCT TCCTCCATTG CCAAGGGCGG     540

GGCTTAGAGC TCAACCCAGA CACCTGTAGG TGCCGGAAGC CGCGAAAGTG A              591

(2) INFORMATION FOR SEQ ID NO:7:

(i) SEQUENCE CHARACTERISTICS:
        (A) LENGTH: 195 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: adult mouse heart (xi) SEQUENCE DESCRIPTION: SEQ ID NO:7:

Met Ser Pro Leu Leu Arg Arg Leu Leu Leu Val Ala Leu Leu Gln Leu
1                5                   10                  15

Ala Arg Thr Gln Ala Pro Val Ser Gln Phe Asp Gly Pro Ser His Gln
            20                  25                  30

Lys Lys Val Val Pro Trp Ile Asp Val Tyr Ala Arg Ala Thr Cys Gln
```

```
              35                  40                  45
Pro Arg Glu Val Val Pro Leu Ser Met Glu Leu Met Gly Asn Val
    50                  55                  60
Val Lys Gln Leu Val Pro Ser Cys Val Thr Val Gln Arg Cys Gly Gly
65                  70                  75                  80
Cys Cys Pro Asp Asp Gly Leu Glu Cys Val Pro Thr Gly Gln His Gln
                85                  90                  95
Val Arg Met Gln Val Pro Gly Pro Met Gly Gln Ile Leu Met Ile Gln
                100                 105                 110
Tyr Pro Ser Ser Gln Leu Gly Glu Met Ser Leu Glu Glu His Ser Gln
                115                 120                 125
Cys Glu Cys Arg Pro Lys Lys Lys Glu Ser Ala Val Lys Pro Asp Ser
130                 135                 140
Pro Arg Ile Leu Cys Pro Pro Cys Thr Gln Arg Arg Gln Arg Pro Asp
145                 150                 155                 160
Pro Arg Thr Cys Arg Cys Arg Cys Arg Arg Arg Arg Phe Leu His Cys
                165                 170                 175
Gln Gly Arg Gly Leu Glu Leu Asn Pro Asp Thr Cys Arg Cys Arg Lys
                180                 185                 190
Pro Arg Lys
        195
```

(2) INFORMATION FOR SEQ ID NO:8:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
ACCATGAGCC CCCTGCTCCG TCGCCTGCTG CTTGTTGCAC TGCTGCAGCT GGCTCGCACC      60
CAGGCCCCTG TGTCCCAGTT TGATGGCCCC AGCCACCAGA AGAAAGTGGT GCCATGGATA     120
GACGTTTATG CACGTGCCAC ATGCCAGCCC AGGGAGGTGG TGGTGCCTCT GAGCATGGAA     180
CTCATGGGCA ATGTGGTCAA ACAACTAGTG CCCAGCTGTG TGACTGTGCA GCGCTGTGGT     240
GGCTGCTGCC CTGACGATGG CCTGGAATGT GTGCCCACTG GCAACACCA  AGTCCGAATG     300
CAGATCCTCA TGATCCAGTA CCCGAGCAGT CAGCTGGGGG AGATGTCCCT GGAAGAACAC     360
AGCCAATGTG AATGCAGACC AAAAAAAAAA AGGAGAGTGC TGTGA                     405
```

(2) INFORMATION FOR SEQ ID NO:9:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Ser Pro Leu Leu Arg Arg Leu Leu Leu Val Ala Leu Leu Gln Leu
1               5                   10                  15
Ala Arg Thr Gln Ala Pro Val Ser Gln Phe Asp Gly Pro Ser His Gln
                20                  25                  30
Lys Lys Val Val Pro Trp Ile Asp Val Tyr Ala Arg Ala Thr Cys Gln
                35                  40                  45
```

```
Pro Arg Glu Val Val Pro Leu Ser Met Glu Leu Met Gly Asn Val
    50                  55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Arg Arg Val Leu
    130
```

(2) INFORMATION FOR SEQ ID NO:10:

(i) SEQUENCE CHARACTERISTICS:
        (A) LENGTH: 570 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (F) TISSUE TYPE: human fibrosarcoma (xi) SEQUENCE DESCRIPTION: SEQ ID NO:10:

```
ACCATGAGCC CTCTGCTCCG CCGCCTGCTG CTCGCCGCAC TCCTGCAGCT GGCCCCCGCC      60
CAGGCCCCTG TCTCCCAGCC TGATGCCCCT GGCCACCAGA GGAAAGTGGT GTCATGGATA     120
GATGTGTATA CTCGCGCTAC CTGCCAGCCC CGGGAGGTGG TGGTGCCCTT GACTGTGGAG     180
CTCATGGGCA CCGTGGCCAA ACAGCTGGTG CCCAGCTGCG TGACTGTGCA GCGCTGTGGT     240
GGCTGCTGCC CTGACGATGG CCTGGAGTGT GTGCCCACTG GGCAGCACCA AGTCCGGATG     300
CAGATCCTCA TGATCCGGTA CCCGAGCAGT CAGCTGGGGG AGATGTCCCT GGAAGAACAC     360
AGCCAGTGTG AATGCAGACC TAAAAAAAAG ACAGTGCTG TGAAGCCAGA CAGCCCCAGG     420
CCCCTCTGCC CACGCTGCAC CCAGCACCAC CAGCGCCCTG ACCCCGGAC CTGCCGCTGC     480
CGCTGCCGAC GCCGCAGCTT CCTCCGTTGC CAAGGGCGGG GCTTAGAGCT CAACCCAGAC     540
ACCTGCAGGT GCCGGAAGCT GCGAAGGTGA                                      570
```

(2) INFORMATION FOR SEQ ID NO:11:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: human fibrosarcoma (xi) SEQUENCE DESCRIPTION: SEQ ID NO:11:

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30
```

```
Arg Lys Val Val Ser Trp Ile Asp Val Tyr Thr Arg Ala Thr Cys Gln
            35                  40                  45

Pro Arg Glu Val Val Pro Leu Thr Val Glu Leu Met Gly Thr Val
 50                  55                  60

Ala Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                 85                  90                  95

Val Arg Met Gln Ile Leu Met Ile Arg Tyr Pro Ser Ser Gln Leu Gly
                100                 105                 110

Glu Met Ser Leu Glu Glu His Ser Gln Cys Glu Cys Arg Pro Lys Lys
                115                 120                 125

Lys Asp Ser Ala Val Lys Pro Asp Ser Pro Arg Pro Leu Cys Pro Arg
            130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
                180                 185
```

(2) INFORMATION FOR SEQ ID NO:12:

(i) SEQUENCE CHARACTERISTICS:
    (A) LENGTH: 624 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (vi) ORIGINAL SOURCE:
    (F) TISSUE TYPE: mouse (xi) SEQUENCE DESCRIPTION: SEQ ID NO:12:

```
ATGAGCCCCC TGCTCCGTCG CCTGCTGCTT GTTGCACTGC TGCAGCTGGC TCGCACCCAG    60

GCCCCTGTGT CCCAGTTTGA TGGCCCCAGC CACCAGAAGA AAGTGGTGCC ATGGATAGAC   120

GTTTATGCAC GTGCCACATG CCAGCCCAGG GAGGTGGTGG TGCCTCTGAG CATGGAACTC   180

ATGGGCAATG TGGTCAAACA ACTAGTGCCC AGCTGTGTGA CTGTGCAGCG CTGTGGTGGC   240

TGCTGCCCTG ACGATGGCCT GGAATGTGTG CCCACTGGGC AACACCAAGT CCGAATGCAG   300

ATCCTCATGA TCCAGTACCC GAGCAGTCAG CTGGGGGAGA TGTCCCTGGA AGAACACAGC   360

CAATGTGAAT GCAGACCAAA AAAAAAGGAG AGTGCTGTGA AGCCAGACAG GGTTGCCATA   420

CCCCACCACC GTCCCCAGCC CCGCTCTGTT CCGGGCTGGG ACTCTACCCC GGGAGCATCC   480

TCCCCAGCTG ACATCATCCA TCCCACTCCA GCCCCAGGAT CCTCTGCCCG CCTTGCACCC   540

AGCGCCGTCA ACGCCCTGAC CCCCGGACCT GCCGCTGCCG CTGCAGACGC CGCCGCTTCC   600

TCCATTGCCA AGGGCGGGGC TTAG                                         624
```

(2) INFORMATION FOR SEQ ID NO:13:

(i) SEQUENCE CHARACTERISTICS:
    (A) LENGTH: 207 amino acids
    (B) TYPE: amino acid
    (D) TOPOLOGY: linear (ii) MOLECULE TYPE: protein (vi) ORIGINAL SOURCE:
    (F) TISSUE TYPE: mouse (xi) SEQUENCE DESCRIPTION: SEQ ID NO:13:

```
Met Ser Pro Leu Leu Arg Arg Leu Leu Leu Val Ala Leu Leu Gln Leu
1               5                   10                  15

Ala Arg Thr Gln Ala Pro Val Ala Gln Phe Asp Gly Pro Ser His Gln
            20                  25                  30

Lys Lys Val Val Pro Trp Ile Asp Val Tyr Ala Arg Ala Thr Cys Gln
            35                  40                  45

Pro Arg Glu Val Val Val Pro Leu Ser Met Glu Leu Met Gly Asn Val
        50                  55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Glu Ser Ala Val Lys Pro Asp Arg Val Ala Ile Pro His His Arg
    130                 135                 140

Pro Gln Pro Arg Ser Val Pro Gly Trp Asp Ser Thr Pro Gly Ala Ser
145                 150                 155                 160

Ser Pro Ala Asp Ile Ile His Pro Thr Pro Ala Pro Gly Ser Ser Ala
                165                 170                 175

Arg Leu Ala Pro Ser Ala Val Asn Ala Leu Thr Pro Gly Pro Ala Ala
            180                 185                 190

Ala Ala Ala Asp Ala Ala Ala Ser Ser Ile Ala Lys Gly Gly Ala
            195                 200                 205
```

(2) INFORMATION FOR SEQ ID NO:14:

(i) SEQUENCE CHARACTERISTICS:
        (A) LENGTH: 624 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (F) TISSUE TYPE: human (xi) SEQUENCE DESCRIPTION: SEQ ID NO:14:

```
ATGAGCCCTC TGCTCCGCCG CCTGCTGCTC GCCGCACTCC TGCAGCTGGC CCCCGCCCAG    60

GCCCCTGTCT CCCAGCCTGA TGCCCCTGGC CACCAGAGGA AAGTGGTGTC ATGGATAGAT   120

GTGTATACTC GCGCTACCTG CCAGCCCCGG GAGGTGGTGG TGCCCTTGAC TGTGGAGCTC   180

ATGGGCACCG TGGCCAAACA GCTGGTGCCC AGCTGCGTGA CTGTGCAGCG CTGTGGTGGC   240

TGCTGCCCTG ACGATGGCCT GGAGTGTGTG CCCACTGGGC AGCACCAAGT CCGGATGCAG   300

ATCCTCATGA TCCGGTACCC GAGCAGTCAG CTGGGGGAGA TGTCCCTGGA AGAACACAGC   360

CAGTGTGAAT GCAGACCTAA AAAAAAGGAC AGTGCTGTGA AGCCAGACAG GGCTGCCACT   420

CCCCACCACC GTCCCCAGCC CCGTTCTGTT CCGGGCTGGG ACTCTGCCCC CGGAGCACCC   480

TCCCCAGCTG ACATCACCCA TCCCACTCCA GCCCCAGGCC CCTCTGCCCA CGCTGCACCC   540

AGCACCACCA GCGCCCTGAC CCCCGGACCT GCCGCCGCCG CTGCCGACGC CGCAGCTTCC   600
```

TCCGTTGCCA AGGGCGGGGC TTAG                                                    624

(2) INFORMATION FOR SEQ ID NO:15:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (vi) ORIGINAL SOURCE:
        (F) TISSUE TYPE: human (xi) SEQUENCE DESCRIPTION: SEQ ID NO:15:

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Pro Leu Thr Val Glu Leu Met Gly Thr Val
50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
            85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Asp Ser Ala Val Lys Pro Asp Arg Ala Ala Thr Pro His His Arg
            130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
            165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
            195                 200                 205

(2) INFORMATION FOR SEQ ID NO:16:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Pro Xaa Cys Val Xaa Xaa Xaa Arg Cys Xaa Gly Cys Cys
1               5                   10

(2) INFORMATION FOR SEQ ID NO:17:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:17:

CACCATGAGC CCTCTGCTCC                                                      20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GCCATGTGTC ACCTTCGCAG                                                      20

(2) INFORMATION FOR SEQ ID NO:19:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Ser Gln Pro Asp Ala Pro Gly His Gln Arg Lys Val Val Ser Trp Ile
1               5                   10                  15

Asp Val Tyr Thr Arg Ala Thr
            20

(2) INFORMATION FOR SEQ ID NO:20:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
            20                  25                  30

Glu Gln Lys Ser His Glu Val Ile Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Glu Lys Pro Ser Cys Val Pro Leu Met
65                  70                  75                  80

Arg Cys Ala Gly Cys Cys Asn Asp Glu Ala Leu Glu Cys Val Pro Thr
                85                  90                  95

Ser Glu Ser Asn Ile Thr Met Gln Ile Met Arg Ile Lys Pro His Gln
            100                 105                 110

Ser Gln His Ile Gly Glu Met Ser Phe Leu Gln His Ser Arg Cys Glu
        115                 120                 125

```
Cys Arg Pro Lys Lys Asp Arg Thr Lys Pro Glu Asn His Cys Glu Pro
    130                 135                 140
Cys Ser Glu Arg Arg Lys His Leu Phe Val Gln Asp Pro Gln Thr Cys
145                 150                 155                 160
Lys Cys Ser Cys Lys Asn Thr Asp Ser Arg Cys Lys Ala Arg Gln Leu
                165                 170                 175
Glu Leu Asn Glu Arg Thr Cys Arg Cys Asp Lys Pro Arg Arg
            180                 185                 190
```

(2) INFORMATION FOR SEQ ID NO:21:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Met Pro Val Met Arg Leu Phe Pro Cys Phe Leu Gln Leu Leu Ala Gly
1               5                   10                  15
Leu Ala Leu Pro Ala Val Pro Pro Gln Gln Trp Ala Leu Ser Ala Gly
            20                  25                  30
Asn Gly Ser Ser Glu Val Glu Val Pro Phe Gln Glu Val Trp Gly
            35                  40                  45
Arg Ser Tyr Cys Arg Ala Leu Glu Arg Leu Val Asp Val Val Ser Glu
50                  55                  60
Tyr Pro Ser Glu Val Glu His Met Phe Ser Pro Ser Cys Val Ser Leu
65                  70                  75                  80
Leu Arg Cys Thr Gly Cys Cys Gly Asp Glu Asn Leu His Cys Val Pro
                85                  90                  95
Val Glu Thr Ala Asn Val Thr Met Gln Leu Leu Lys Ile Arg Ser Gly
                100                 105                 110
Asp Arg Pro Ser Tyr Val Glu Leu Thr Phe Ser Gln His Val Arg Cys
            115                 120                 125
Glu Cys Arg Pro Leu Arg Glu Lys Met Lys Pro Glu Arg Cys Gly Asp
    130                 135                 140
Ala Val Pro Arg Arg
145
```

(2) INFORMATION FOR SEQ ID NO:22:

(i) SEQUENCE CHARACTERISTICS:
        (A) LENGTH: 196 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Met Arg Thr Trp Ala Cys Leu Leu Leu Gly Cys Gly Tyr Leu Ala
1               5                   10              15
His Ala Leu Ala Glu Glu Ala Glu Ile Pro Arg Glu Leu Ile Glu Arg
            20                  25                  30
Leu Ala Arg Ser Gln Ile His Ser Ile Arg Asp Leu Gln Arg Leu Leu
            35                  40                  45
Glu Ile Asp Ser Val Gly Ala Glu Asp Ala Leu Glu Thr Ser Leu Arg
50                  55                  60
```

Ala His Gly Ser His Ala Ile Asn His Val Pro Glu Lys Arg Pro Val
65                  70                  75                  80

Pro Ile Arg Arg Lys Arg Ser Ile Glu Glu Ala Ile Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Ser Asn Leu Asn Pro Asp His Arg Glu Glu Glu
            180                 185                 190

Thr Asp Val Arg
        195

(2) INFORMATION FOR SEQ ID NO:23:

(i) SEQUENCE CHARACTERISTICS:
        (A) LENGTH: 241 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

Met Asn Arg Cys Trp Ala Leu Phe Leu Pro Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Arg Asp Ser Val Asp Glu Asp Gly Ala Glu Leu Asp Leu Asn Met
50                  55                  60

Thr Arg Ala His Ser Gly Val Glu Leu Glu Ser Ser Arg Gly Arg
65                  70                  75                  80

Arg Ser Leu Gly Ser Leu Ala Ala Ala Glu Pro Ala Val Ile Ala Glu
                85                  90                  95

Cys Lys Thr Arg Thr Glu Val Phe Gln Ile Ser Arg Asn Leu Ile Asp
            100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Ala Ser
130                 135                 140

Gln Val Gln Met Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Ile Val Thr Pro Arg Pro Val Thr Arg Ser
            180                 185                 190

Pro Gly Thr Ser Arg Glu Gln Arg Ala Lys Thr Pro Gln Ala Arg Val
        195                 200                 205

Thr Ile Arg Thr Val Arg Ile Arg Arg Pro Pro Lys Gly Lys His Arg

-continued

```
                210                 215                 220
Lys Phe Lys His Thr His Asp Lys Ala Ala Leu Lys Glu Thr Leu Gly
225                 230                 235                 240
Ala
```